(12) United States Patent
Austin et al.

(10) Patent No.: US 10,274,461 B2
(45) Date of Patent: *Apr. 30, 2019

(54) NANOCHANNEL ARRAYS AND THEIR PREPARATION AND USE FOR HIGH THROUGHPUT MACROMOLECULAR ANALYSIS

(71) Applicant: The Trustees of Princeton University, Princeton, NJ (US)

(72) Inventors: Robert H. Austin, Princeton, NJ (US); Zhaoning Yu, Palo Alto, CA (US); Jonas O. Tagenfeldt, Lund (SE); Stephen Y. Chou, Princeton, NJ (US); Han Cao, San Diego, CA (US)

(73) Assignee: The Trustees of Princeton University, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/621,271

(22) Filed: Jun. 13, 2017

(65) Prior Publication Data

US 2017/0343509 A1    Nov. 30, 2017

Related U.S. Application Data

(60) Continuation of application No. 14/081,322, filed on Nov. 15, 2013, now Pat. No. 9,678,038, which is a continuation of application No. 12/261,406, filed on Oct. 30, 2008, now Pat. No. 8,652,828, which is a division of application No. 10/484,293, filed as application No. PCT/US02/23610 on Jul. 25, 2002, now Pat. No. 7,670,770.

(Continued)

(51) Int. Cl.
*G01N 27/447* (2006.01)

(52) U.S. Cl.
CPC ..... *G01N 27/44791* (2013.01); *G01N 27/447* (2013.01)

(58) Field of Classification Search
CPC ................................................ G01N 27/44791
See application file for complete search history.

(56) References Cited

U.S. PATENT DOCUMENTS 5,314,829 A    5/1994    Coles
5,356,776 A    10/1994    Kambara et al.
(Continued)

FOREIGN PATENT DOCUMENTS

WO    1998035012    8/1998
WO    1998052691    11/1998
(Continued)

OTHER PUBLICATIONS

C.-F. Chou, et al. "Sorting biomolecules with microdevices" Electrophoresis vol. 21, Jan. 2000, p. 81-90.*
(Continued)

*Primary Examiner* — J. Christopher Ball
(74) *Attorney, Agent, or Firm* — Riverside Law LLP

(57) ABSTRACT

Nanochannel arrays that enable high-throughput macromolecular analysis are disclosed. Also disclosed are methods of preparing nanochannel arrays and nanofluidic chips. Methods of analyzing macromolecules, such as entire strands of genomic DNA, are also disclosed, as well as systems for carrying out these methods.

33 Claims, 10 Drawing Sheets

Related U.S. Application Data

(60) Provisional application No. 60/307,668, filed on Jul. 25, 2001.

(56) References Cited

U.S. PATENT DOCUMENTS

| | | | |
|---|---|---|---|
| 5,427,663 A * | 6/1995 | Austin | B01J 19/0093 204/450 |
| 5,560,811 A | 10/1996 | Briggs et al. | |
| 5,612,181 A | 3/1997 | Fourmentin-Guilbert | |
| 5,772,905 A | 6/1998 | Chou | |
| 5,814,444 A | 9/1998 | Rabinovitch | |
| 5,843,767 A | 12/1998 | Beattie | |
| 5,867,266 A | 2/1999 | Craighead | |
| 5,882,465 A | 3/1999 | McReynolds | |
| 5,976,444 A | 11/1999 | Pearson et al. | |
| 6,083,758 A | 7/2000 | Imperiali et al. | |
| 6,110,339 A | 8/2000 | Yager et al. | |
| 6,165,688 A | 12/2000 | Celotta et al. | |
| 6,182,733 B1 | 2/2001 | McReynolds | |
| 6,185,961 B1 | 2/2001 | Tonucci et al. | |
| 6,210,896 B1 | 4/2001 | Chan | |
| 6,214,246 B1 | 4/2001 | Craighead | |
| 6,263,286 B1 | 7/2001 | Gilmanshin et al. | |
| 6,304,318 B1 | 10/2001 | Matsumoto | |
| 6,309,580 B1 | 10/2001 | Chou | |
| 6,334,960 B1 | 1/2002 | Wilson et al. | |
| 6,355,420 B1 | 3/2002 | Chan | |
| 6,403,311 B1 | 6/2002 | Chan | |
| 6,438,279 B1 | 8/2002 | Craighead et al. | |
| 6,440,662 B1 | 8/2002 | Gerwen et al. | |
| 6,482,742 B1 | 11/2002 | Chou | |
| 6,515,751 B1 | 2/2003 | Craighead et al. | |
| 6,518,189 B1 | 2/2003 | Chou | |
| 6,635,163 B1 | 10/2003 | Han et al. | |
| 6,685,847 B2 | 2/2004 | Sadayama | |
| 6,696,022 B1 | 2/2004 | Chan et al. | |
| 6,755,621 B2 | 6/2004 | Lopez et al. | |
| 6,762,059 B2 | 7/2004 | Chan et al. | |
| 7,056,661 B2 | 6/2006 | Korlach et al. | |
| 7,217,562 B2 | 5/2007 | Cao et al. | |
| 8,722,327 B2 | 5/2014 | Han et al. | |
| 2001/0014850 A1 | 8/2001 | Gilmanshin et al. | |
| 2001/0045357 A1 | 11/2001 | Broadley et al. | |
| 2002/0015149 A1 | 2/2002 | Rahbar-Dehghan et al. | |
| 2002/0028451 A1 | 3/2002 | Abbott et al. | |
| 2002/0039737 A1 | 4/2002 | Chan et al. | |
| 2002/0042027 A1 | 4/2002 | Chou et al. | |
| 2002/0072243 A1 | 6/2002 | Craighead et al. | |
| 2002/0081744 A1 | 6/2002 | Chan et al. | |
| 2002/0132482 A1 | 9/2002 | Chou | |
| 2002/0160356 A1 | 10/2002 | Craighead et al. | |
| 2002/0167117 A1 | 11/2002 | Chou | |
| 2003/0012657 A1 | 1/2003 | Marr et al. | |
| 2003/0012866 A1 | 1/2003 | Harnett et al. | |
| 2003/0013186 A1 | 1/2003 | Martin et al. | |
| 2003/0034329 A1 | 2/2003 | Chou | |
| 2003/0080471 A1 | 5/2003 | Chou | |
| 2003/0080472 A1 | 5/2003 | Chou | |
| 2003/0170995 A1 | 9/2003 | Chou | |
| 2003/0170996 A1 | 9/2003 | Chou | |
| 2004/0011647 A1 | 1/2004 | Broadley et al. | |
| 2004/0033515 A1 | 2/2004 | Cao et al. | |
| 2004/0197843 A1 | 10/2004 | Chou et al. | |
| 2005/0023156 A1 | 2/2005 | Ramsey et al. | |
| 2008/0242556 A1 | 10/2008 | Cao et al. | |
| 2013/0186757 A1 | 7/2013 | Reinhart et al. | |
| 2015/0136601 A1 | 5/2015 | Austin et al. | |

FOREIGN PATENT DOCUMENTS

| | | |
|---|---|---|
| WO | 1999012016 | 3/1999 |
| WO | 2000000868 | 1/2000 |
| WO | 2000009757 | 2/2000 |
| WO | 2000042233 | 7/2000 |
| WO | 2001018246 | 3/2001 |
| WO | 2001027610 | 4/2001 |
| WO | 2001037958 | 5/2001 |
| WO | 2002007199 | 1/2002 |
| WO | 2003010289 | 2/2003 |
| WO | 2003079416 | 9/2003 |
| WO | 2003106693 | 12/2003 |

OTHER PUBLICATIONS

Akeson, et al., "Microsecond time-scale discrimination among polycytidylic acid, polyadenylic acid, and polyuridylic acid as homopolymers or as segments within single RNA molecules," Biophysical J, 77:3227-3233, 1999 Anonymous, "The personal genome sequencer," Technology Review, 76-79, 2002 Austin, "Fabrication of a molecular self-assembled monolayer diode using nanoimprint lithography," Nano Letters, 3 (12):1687-1690, 2003.

Anonymous, "The personal genome sequencer," Technology Review, 76-79, 2002.

Austin, "Fabrication of a molecular self-assembled monolayer diode using nanoimprint lithography," Nano Letters, 3 (12):1687-1690, 2003.

Austin, et al., "Fabrication of 70nm channel length polymer organic thin-film transistors using nanoimprint lithography," Applied Physics Letts, 81(23):4431-4433, 2002.

Austin, et al., "Fabrication of nanocontacts for molecular devices using nanoimprint lithography," J Vac Sci Technol B, 20(2):665-667, 2002.

Austin, et al., "Scanning the controls: genomics and nanotechnology," IEEE Trans On Nanotechnology, 99(1):12-18, 2002.

Bakajin, "Separation of 100-kilobase DNA molecules in 10 seconds," Anal Chem, 73(24): 6053-6056, 2001.

Ball, "DNA combed into nanochannels," NPG Nature Publishing Group. 2002. Web. http://www.nature.com.

Bates, et al., "Dynamics of DNA molecules in a membrane channel probed by active control techniques," Biophysical J, 84:2366-2372, 2003.

Bhusari, et al., "Fabrication of air-channel structures for microfluidic, microelectromechanical, and microelectronic applications," J of Microelectromech Syst,10(3):400-408, 2001.

Braslavsky, et al., "Sequence information can be obtained from single DNA molecules," PNAS. 2003. 100 (7):3960-3964.

Cao, "Sensors and Sensitivity," Innovation, The Princeton Journal of Science and Technology, 28-31, 2002.

Cao, et al., "Fabrication of 10 nm enclosed nanofluidic channels," Applied Physics Letters, 81(1):174-176, 2002.

Cao, et al., "Gradient nanostructures for interfacing microfluidics and nanofluidics," Apllied Physics Letters, 81 (16):3058-3060, 2002.

Chou et al., "Imprint lithography with 25-nanometer resolution," Science, 272:85-87, 1996.

Chou et al., "Imprint of sub-25 nm vias and trenches in polymers," Appl. Phys. Lett, 67(21):3114-3116, 1995.

Chou, "Imprint lithography with sub-10 nm feature size and high throughput," Microelectronic Eng, 35:237-240, 1997.

Chou, "Patterned magnetic nanostructures and quantized magnetic disks," Proceedings of the IEEE, 85(4):652-671, 1997.

Chou, et al. "Sorting biomolecules with microdevices," Electrophoresis, 21:81-90, 2000.

Chou, et al., "A microfabricated device for sizing and sorting DNA molecules," Proc Nat Acad Sci USA, 96:11-13, 1999.

Chou, et al., "Sorting by diffusion: an asymmetric obstacle course for continuous molecular separation," PNAS, 96 (24):13762-13765,1999.

Chou, et al., "Ultrafast and direct imprint of nanostructures in silicon," Nature, 417:835-837, 2002.

Cui, et al., "Perpendicular quantized magnetic disks with 45 Gbits on a 4 x 4 cm2 area," J of Applied Physics, 85 (8):5534-5536, 1999.

Dumbravescu, "Smooth 3-D shaping of thick resists by means of gray tone lithography", IEEE, 217-220, 1999.

(56) References Cited

OTHER PUBLICATIONS

Foquet, et al., "DNA fragment sizing by single molecule detection in submicrometer-sized closed fluidic channels," Analytical Chem, 74(6):1415-1422, 2002.
GenomeWeb.com, "Nanochannel tech offers promise for cheap, quick DNA analysis chips: Startup to Launch", 2002.
Gerstner, "Put a lid on it!," NPG Nature Publishing Group, Web. http://www.nature.com, 2002.
Guo, et al., "Nanoscale silicon field effect transistors fabricated using imprint lithography," Appl Phys Lett, 71 (13)1881-1883, 1997.
Hamley et al., "Structure and flow behaviour of block copolymers," J of Physics: Condensed Matte, 13:R643-R671, 2001.
Han, et al. "Entropic trapping and sieving of long DNA molecules in a nanofluidic channel," J Vac Sci Technol A, 17 (4):2142-2147, 1999.
Han, et al., "Characterization and optimization of an entropic trap for DNA separation," Analytical Chem, 74: 394-401, 2002.
Han, et al., "From microfluidics to nanofluidics: DNA separation using nanofluidic entropic trap array device," Microfluidic Devices and Systems III, Proceedings of SPIE, Mastrangelo, C.H., et al. (Eds.), 4177:42-48, 2000.
Han, et al., "Separation of long DNA molecules in a microfabricated entropic trap array," Science, 288:1026-1029, 2000.
Harnett, et al., "Heat-depolymerizable polycarbonates as electron beam patternable sacrificial layers for nanofluidics,"J Vac Scie Technol B, 19(6):2842-2845, 2001.
Harrison et al., "Lithography with a mask of a block copolymer microstructures", J Vac Sci Technol B, 16(2): 544-552, 1998.
Henke et al., "Simulation and experimental study of gray-tone lithography for the fabrication of arbitrarily shaped surfaces", IEEE, 205-210, 1994.
Henrickson, et al., "Driven DNA transport into an asymmetric nanometer-scale pore," Physical Review Letters, 85 (14):3057-3060, 2000.
Holmes et al., "Estimation of polyacrylamide gel pore size from Ferguson plots of normal and anomalously migrating DNA fragments. I. Gels containing 3% N,N'3 -methylenebisacrylamide", Electrophoresis, 12(4): 253-263, 1991.
Huang et al., "Nanodomain control in copolymer thin films" Nature, 395: 767-768, 1998.
Ju, et al., "Molecular dynamics stimulation of sputter trench-fillnig morphology in damascene process," J Vac Sci Technol B, 20(3):946-955, 2002.
Kalaugher, "Diffraction gradient lithography aids nanofluidics," IOP Publishers Nanotechnology, Web, http://nanotechweb.org, 2003.
Kasianowicz, et al., "Characterization of individual polynucleotide molecules using a membrane channel," Proc Natl Acad Scie USA. 1996. 93:13770-13773, 1996.
Kong et al., "Fabrication, writing, and reading of 10 Gbits/in2 longitudinal quantized magnetic disks with a switching field over 1000 Oe," Jpn J Appl Phys, 37:5973-5975, 1998.
Kong, "Magnetotransport and domain structures in nanoscale NiFe/Cu/Co spin valve," J of Applied Physics, 85 (8):5492-5494, 1999.
Kong, et al., "Writing and reading 7.5 Gbits/in2 longitudinal quantized magnetic disk using magnetic force microscope tips," IEEE Transactions on Magnetics, 33(5):3019-3021, 1997.
Krauss, et al., "Fabrication of planar quantum magnetic disk structure using electron beam lithography, reactive ion etching, and chemical mechanical polishing," J Vac Sci Technol B, 13(6):2850-2852, 1995.
Krauss, et al., "Nano-compact disks with 400 Gbit/in2 storage density fabricated using nanoimprint lithography and read with proximal probe," Appl Phys Lett, 71(21):3174-3176, 1997.
Li, et al., "Direct three-dimensional patterning using nanoimprint lithography," Applied Physics Letts, 78(21):3322-3324, 2001.
Li, et al., "Fabrication of circular optical structures with a 20 nm minimum feature size using nanoimprint lithography," Applied Physics Letts, 76(6):673-675, 2000.

Li, et al., "Ion-beam sculpting at nanometer length scales," Nature, 412:166-169, 2001.
Li, et al., "Large area direct nanoimprinting of SiO2—Ti—O2 gel gratings for optical applications," J Vac Sci Tchnol B, 21 (2):660-663, 2003.
Li, et al., "Pattern transfer fidelity of nanoimprint lithography on six-inch wafers," Nanotechnology, 14:33-36, 2003.
Li, et al., "Sacrificial polymers for nanofluidic channels in biological applications," Nanotechnology, 14:578-583, 2003.
Mason, "Princeton builds tiniest tunnel, reveals nanostamping process," Smalltimes, www.smalltimes.com, 2003.
Masuda, et al., "Highly ordered nanochannel-array architecture in anodic alumina," Am Inst of Physics, 2770-2772, 1997.
Meller, "Dynamics of polynucleotide transport through nanometer-scale pores," J Phys Condens Matter, 15:R581-R607, 2003.
Meller, "Rapid nanopore discrimination between single polynucleotide molecules," PNAS, 97(3):1079-1084, 2000.
Meller, et al., "Single molecule measurements of DNA transport through a nanopore," Electrophoresis, 23:2583-2591, 2002.
Meller, et al., "Voltage-driven DNA translocations through a nanopore," Am Physic Soc, 86(15):3435-3438, 2001.
Morkved, et al., "Local Control of microdomain orientation in diblock copolymer thin films with electric fields," Science, 273(5277):931-933, 1996.
Morrow et al., "Novel system zero in on the $100 genome", GEN, 29(8), 2009.
Perry, et al., "Review of fabrication of nanochannels for single phase liquid flow," Proceedings of ICMM, 1-8, 2005.
Quake, et al., "From micro- to nanofabrication with soft materials," Science, 290:1536-1540, 2000.
Riordan, "Patents: An obsession with DNA and the human genome leads to development of a technology," New York Times, 2002.
Schultz, "Accidental discovery—New technique coaxes structures to assemble themselves," Princeton University, Web, http://www.princeton.edu/~seasweb/eqnews/spring00/feature2.html, 2005.
Schultz, "Discover could lead to faster, smaller, cheaper computer chips," Princeton University, http://www.princeton.edu, 2003.
Shaw, "Separation of large DNA molecules by Pulsed Field Gel Electrophoresis", 1992, Methods in Molecular Biology, 13, Protocols in Molecular Neurobiology, Edited by: A. Longstaff and P. Revest, The Humane Press, Totowa, NJ, Cahpter 1, pp. 1-13 (1992).
Soares, et al., "Fabrication of dielectric hollow submicrometric pipes," J Vac Scie Technol B, 713-716, 2000.
Stern, et al., "Nanochannel fabrication for chemical sensors," J Vac Scie Technol B, 15(6):2887-2891, 1997.
Stikeman, "Nanobiotech Makes the diagnosis," Technology Review, 61-66, 2002.
Stjernstrom, et al., "Method for fabrication of microfluidic systems in glass," J Micromech and Microeng, 8:33-38, 1998.
Strum, "Multidisciplinary development of platforms for protein identification, expression and control at the single cell level in the post genomics era," Princeton University, http://www.darpa.mil/dso/thrust/biosci/bim/princeton.html. Web, 2005.
Sun, et al., "Multilayer resist methods for nanoimprint lithography on nonflat surfaces," J Vac Sci Technol B, 16 (6):3922-3925, 1998.
Tan, et al., "Roller nanoimprint lithography," J Vac Sci Technol B, 16(6):3926-3928, 1998.
Tegenfeldt, et al., "Micro- and nanofluidics for DNA analysis," Anal Bioanal Chem, 378: 1678-1692, 2004.
Tegenfeldt, et al., "Near-field scanner for moving molecules," Phys Rev Lett, 86(7):1378-1381, 2001.
Thornell et al., "Microprocessing at the fingertips", J Micromech Microeng, 8: 251-262, 1998.
Turner et al., "Monolithic fabrication of nanofluidic artificial gel media for DNA electrophoresis", Proc. SPIE 3258, Micro- and Nanofabricated Structures and Devices for Biomedical Environmental Applications, 3258: 114-121, 1998.
Turner, et al., "Solid State Artificial Gel for DNA Electrophoresis with an Integrated Top Layer", Hournal Vacuum Science, B 16 (6):3835-3840, 1998.
Turner, et al., "Confinement-induced entropic recoil of single DNA molecules in a nanofluidic structure," The Am Physical Soc, 88(12):128103-1-128103-4, 2002.

(56) References Cited

OTHER PUBLICATIONS

Turner, et al., "Monolithic nanofluid sieving structures for DNA manipulation," J Vac Sci Technol B, 16(6):3835-3840, 1998.

Vercoutere, et al., "Rapid discrimination among individual DNA hairpin molecules at single-nucleotide resolution using an ion channel," Nature Biotechnology, 19:248-252, 2001.

Wang et al., "Direct nanoimprint of submicron organic light-emitting structures," Applied Physics Letts, 75 (18):2767-2769, 1999.

Wang et al., "Fabrication of a new broadband waveguide polarizer with a double-layer 190 nm period metal-gratings using nanoimprint lithography," J Vac Sci Technol B,17(6):2957-2960, 1999.

Wang, et al., "Molecular alignment in submicron patterned polymer matrix using nanoimprint lithography," Applied Physics Letts, 77(2):166-168, 2000.

Wheeler et al., "Information on DNA conformation derived from transverse pore gradient gel electrophoresis in conjunction with an advanced data analysis applied to capillary electrophoresis in polymer media", Electrophoresis, 13:604-608, 1992.

Wu, et al., "Large area high density quantized magnetic disks fabricated using nanoimprint lithography," J Vac Sci Technol B, 16(6):3825-3829, 1998.

Wu, et al., "Room-temperature Si single-electron memory fabricated by nanoimprint lithography," Applied Physics Letts, 83(11):2268-2270, 2003.

www.economist.com, "Stamping on tradition," Science and Technology, 2002.

www.ee.princeton.edu, "Various pages downloaded from www.ee.princetonedu/~chouweb," Web, 2002.

www.physics.ucsb.edu, "AFM of single-stranded RNA, triple-stranded DNA and helix", Web, 2002.

www.uic.edu, "Mechanical (and statistical-mechanical) properties of biofilaments," Web, 2002.

www.usgenomics.com, "U.S. genomics awarded patent using fluorophores in direct, linear DNA analysis," U.S. Genomics, 2001.

www.usgenomics.com, "U.S. genomics awarded pioneering patent for direct, linear DNA analysis," U.S. Genomics, 2002.

Xia, et al., "Ultrafast patterning of nanostructures in polymers using laser assisted nanoimprint lithography," Applied Physics Letts, 83(21):4417-4419, 2003.

Yu et al., "Fabrication of large area 100 nm pitch grating by spatial frequency doubling and nanoimprint lithography for subwavelength optical applications," J Vac Sci Technol B, 19(6):2816-2819, 2001.

Yu et al., "Fabrication of nanoscale gratings with reduced line edge roughness using nanoimprint lithography," J Vac Sci Technol B, 21(5):2089-2092, 2003.

Yu, et al., "Fabrication of large area subwavelength antireflection structures on Si using trilayer resist nanoimprint lithography and liftoff," J Vac Sci Technol B, 21(6):2874-2877, 2003.

Yu, et al., "Nanoscale GaAs metal-semiconductor-metal photodetectors fabricated using nanoimprint lithography," Applied Physics Letts, 74(16):2381-2383, 1999.

Yu, et al., "Reflective polarizer based on a stacked double-layer subwavelength metal grating structure fabricated using nanoimprint lithography," Appl Phys Letts, 77(7):927-929, 2000.

Zhang, et al., "Fabrication of 60-nm transistors on 4-in. wafer using nanoimprint at all lithography levels," Applied Physics Letts, 83(8):1632-1634, 2003.

Zhang, et al., "Multilevel nanoimprint lithography with submicron alignment over 4 in. Si wafers," Applied Physics Letts, 79(6):845-847, 2001.

\* cited by examiner

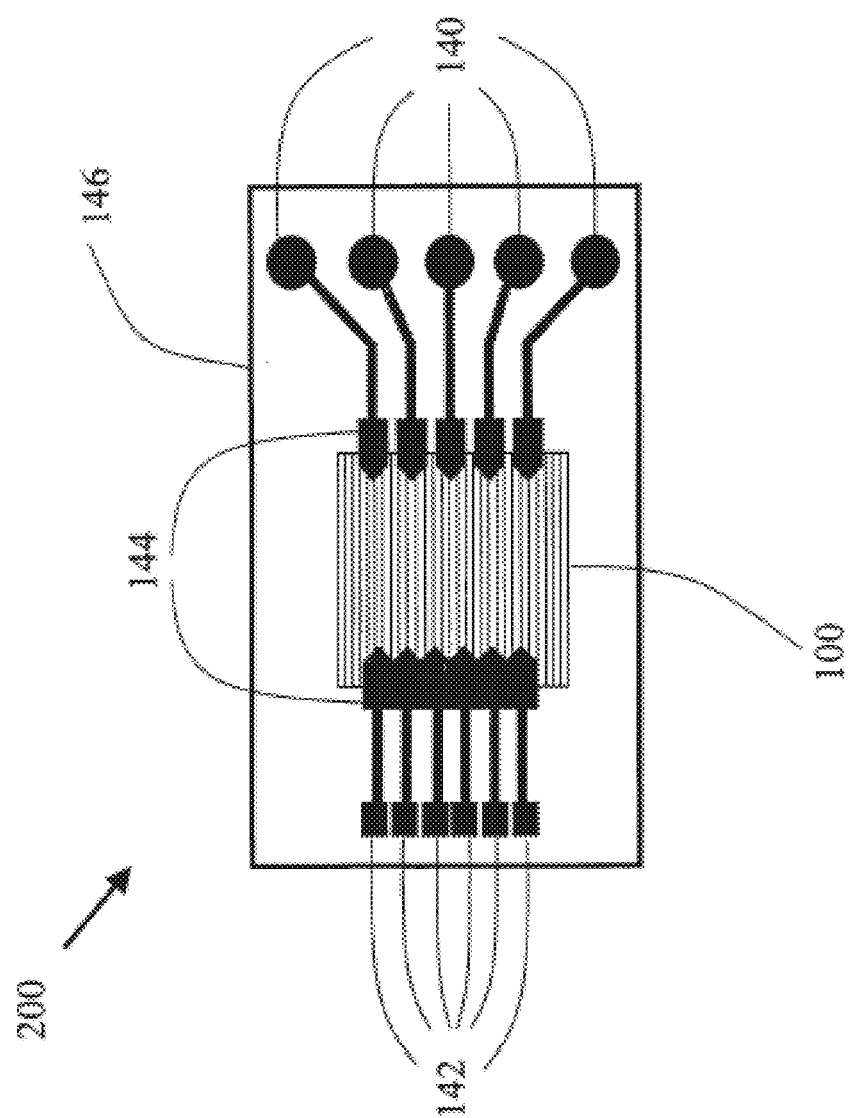

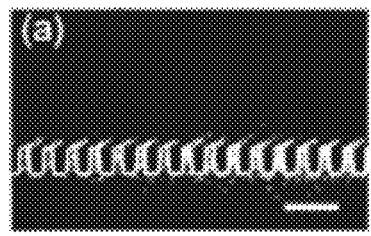
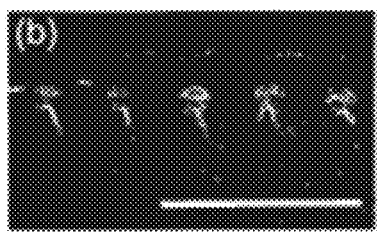
FIG. 7A  FIG. 7B
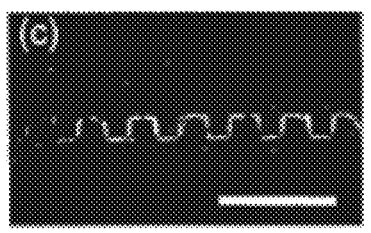
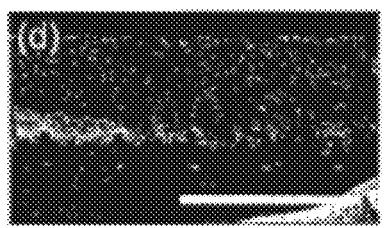
FIG. 7C  FIG. 7D
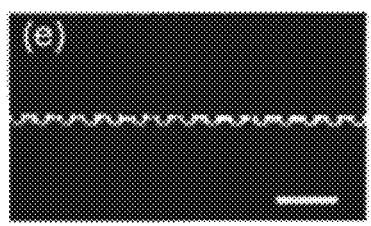
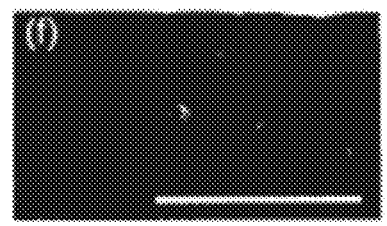
FIG. 7E  FIG. 7F

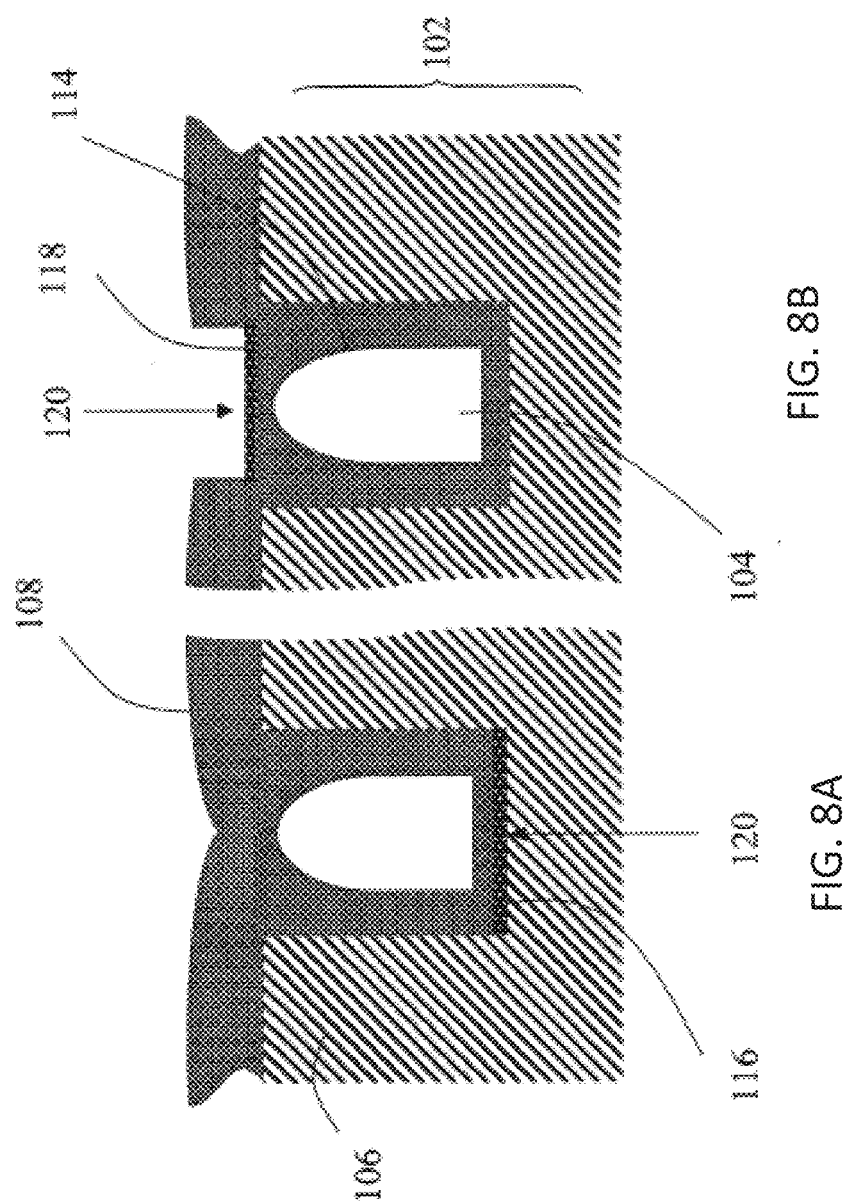

NANOCHANNEL ARRAYS AND THEIR PREPARATION AND USE FOR HIGH THROUGHPUT MACROMOLECULAR ANALYSIS

CROSS-REFERENCE TO RELATED APPLICATIONS

The present application is a continuation application of U.S. patent application Ser. No. 14/081,322, filed Nov. 15, 2013, now issued as U.S. Pat. No. 9,678,038, which is a continuation application of U.S. patent application Ser. No. 12/261,406, filed Oct. 30, 2008, now issued as U.S. Pat. No. 8,652,828, which is a divisional application of U.S. patent application Ser. No. 10/484,293, filed Jan. 20, 2004, now issued as U.S. Pat. No. 7,670,770, which is the U.S. national phase application filed under 35 U.S.C. § 371 claiming benefit to International Patent Application No. PCT/US02/23610, filed Jul. 25, 2002, which is entitled to priority under 35 U.S.C. § 119(e) to U.S. Provisional application No. 60/307,668, filed Jul. 25, 2001, each of which are incorporated herein by reference in their entireties.

STATEMENT OF GOVERNMENT SUPPORT

This invention was made with government support under DARPA Grant Number MDA972-00-1-0031 awarded by the Defense Advanced Research Projects Agency. The government has certain rights in the invention.

BACKGROUND

The present invention relates to a nanochannel array. The present invention also relates to a method of preparing nanochannel arrays. The present invention also relates to nanofluidic chips containing nanochannel arrays. The present invention also relates to a system suitable for high throughput analysis of macromolecules. The present invention also relates to a method of analyzing as least one macromolecule by using a nanochannel array.

In the newly emerging field of bionanotechnology, extremely small nanofluidic structures, such as channels, need to be fabricated and used as arrays for the manipulation and analysis of biomolecules such as DNA and proteins at single molecule resolution. In principle, the size of the cross sectional area of channels should be on the order of the cross sectional area of elongated biomolecules, i.e., on the order of 1 to 100 square nanometers, to provide elongated (e.g., linear, unfolded) biomolecules that can be individually isolated, yet analyzed simultaneously by the hundreds, thousands, or even millions. Likewise, it is also desirable that the length of the channels should be long enough to accommodate the longest of macromolecules, such as an entire chromosome, which can be on the order of 10 centimeters long (e.g., chromosome 1 of the human genome having 250 million base pairs). The present inventors and others have recently been concerned about such problems and their possible solutions, as reported in: O. Bakajin, et al., *Anal. Chem.* 73 (24), 6053 (2001), J. O. Tegenfeldt, et al., *Phys. Rev. Lett.* 86 (7), 1378 (2001), J. Han et al., *Science* 288, 1026 (2000), and S. R. Quake et al., *Science* 290 (5496), 1536 (2000).

It is important to efficiently and reliably construct arrays of many thousands, or even millions of channels in an array for the simultaneous isolation and analysis of up to thousands or millions of individual macromolecules. Such large arrays of isolated macromolecules could, in principle, be analyzed with presently available two-dimensional area detectors, such as charge-coupled devices (CCDs). Together with automated data-processing collection and image analysis software, the simultaneous characterization of up to thousands or millions of macromolecules would be an extremely powerful tool for macromolecular analysis, such as population distribution analysis of macromolecular size, chemical composition, and DNA sequencing.

Because individual macromolecules could in principle be isolated and analyzed in a single channel, heterogeneity of a sample containing a multitude of macromolecules can be readily discerned. This would be particularly useful for identifying single nucleotide polymorphisms (SNP) on a single chromosome. In contrast, traditional population based assays require time-consuming DNA amplification methods to prepare multiple copies of a nucleic acid macromolecule to carry out SNP analysis. If available, a chromosomal analysis system incorporating nanochannel arrays could perform SNP analysis much more quickly than my method presently available.

Nanochannel arrays having the proper dimensions for carrying out the simultaneous isolation and analysis of a multitude of elongated macromolecules have been heretofore unavailable. Accordingly, there is an urgent need to provide nanochannel arrays having at least three key dimensional qualities: (1) the channels should have a sufficiently small dimension to elongate and isolate macromolecules; (2) the channels should have a sufficiently long dimension to permit of the instantaneous observation of the entire elongated macromolecule; and (3) a high number of channels should be provided to permit the simultaneous observation of a high number of macromolecules. In addition, it would be desirable for the elongated and isolated macromolecules to remain indefinitely in such a state at ambient conditions even after the field which is used to transport the macromolecules into the channels (e.g., electric field) is turned off. This feature would permit the macromolecules to be analyzed with techniques that require times longer than the residence time of the macromolecule under the influence of the field. This feature would also permit analysis of macromolecules without having to subject them to a field.

Methods for analyzing macromolecules (e.g., polymers) have been previously disclosed, however none uses a nanochannel array having the three key dimensional qualities as described supra. U.S. Pat. No. 5,867,266 discloses a micro optical system having a plurality of coplanar micron-to-millimeter scale sample channels prepared using photolithography and an artificial gel material comprising a multiplicity of pillar structures in each micron-to-millimeter wide sample channel. The large channel width makes this system unsuitable as a nanochannel array.

Likewise, methods for analyzing macromolecules (e.g., polymers) by isolating them in channels more narrow than this disclosed in U.S. Pat. No. 5,867,266, however none uses a nanochannel array having the three key dimensional qualities as described supra. In WO 00/09757, several of the inventors of the present patent application disclose a system for optically characterizing single polymers that are transported in a straightened form through a channel. In U.S. Pat. No. 6,355,420, a system is disclosed for analyzing polymers that are transported in a straightened form through a plurality of (at least 50) channels. While both of these disclosures are directed towards analysis of single macromolecules aligned in one or more channels, neither of these documents discloses the simultaneous observation of a high number of macromolecules in a multitude of channels.

Thus, there remains the problem of providing suitable nanochannel arrays that are useful in a variety of macromolecular analysis. Methods for analyzing macromolecules (e.g., polymers) by isolating them in a narrow channel have been previously disclosed, however none uses a nanochannel array having the three key dimensional qualities as described supra, primarily because, until now, fabrication techniques for constructing such a nanochannel array were not available.

In creating ultra-small nanofluidic structures, e.g. for single biomolecule analysis, at least two problems need to be solved: reduction of size and creation of sealed fluidic channels. As reported by one of the present inventors, NIL is a parallel high-throughput technique that makes it possible to create nanometer-scale features over large substrate surface areas at low cost (S. Y. Chou et al., *Appl. Phys. Lett.* 67 (21), 3114 (1995) and S. Y. Chou et al., *Science* 272, 85 (1996)) Current sealing techniques such as wafer bonding (M. Stjernstrom et al., *J. Micromech. and Microeng.* 8 (1), 33 (1998)), and soft elastomer sealing (H. P. Chou et al., *Proc. Nat. Acad. Sci. USA* 96 (1), 11 (1999), are suitable for relatively large planar surfaces and provide as effective seal. Wafer bonding requires an absolutely defect free and flat surface, and elastomer sealing suffers from clogging due to soft material intrusion into the channels. Within extremely small confining structures, biological samples are also much more sensitive to issues such as hydrophobicity and the homogeneity of the material constructing the fluidic structure.

Recently developed techniques using "place-holding" sacrificial materials such as polysilicon (S. W. Turner et al., *J. Vac. Sci. and Technol.* B 16(6), 3835 (1998)) and polynorbornene (D. Bhusari et al., *J. Microelectromech. Syst.* 10 (3), 400 (2001)) have gained popularity to create sealed small hollow fluidic structures. However, steps needed in removing the sacrificial materials such as heating the substrate up to 200-400° C. or wet etching limits the use of certain materials and downstream fabrication processes.

As provided herein, the present invention achieves the goal of providing nanochannel arrays suitable for performing high throughput macromolecular analysis. Interferometric lithography (IL), nanoimprint lithography (NIL), and non-isotropic deposition techniques are used to prepare nanochannel arrays having hundreds of thousands to more than a million enclosed channels having the desired key dimensions across the surface of a silicon wafer substrate.

In one aspect of the present invention, there are provided nanochannel arrays including a surface having a plurality of channels in the material of the surface, said channels having a trench width of less than about 150 nanometers and a trench depth of less than 200 nanometers; at least some of the channels being surmounted by sealing material to render such channels at least substantially enclosed.

In a further aspect of the present invention, methods of preparing nanochannel arrays are disclosed, which include the steps of: providing a substrate having a surface; forming a plurality of channels in the material of the surface; and depositing a sealing material on the plurality of channels to surmount the plurality of channels to render such channels at least substantially enclosed, the substantially enclosed channels having a trench width of less than 150 nanometers and a trench depth of less than 200 nanometers.

In another aspect of the invention, there are provided nanofluidic chips including: a) nanochannel array, including: a substrate having a surface; a plurality of parallel channels in the material of the surface, said channels having a trench width of less than about 150 nanometers and a trench depth of less than 200 nanometers; at least some of the channels being surmounted by sealing material to render such channels at least substantially enclosed; at least some of the channels are capable of admitting a fluid; b) at least one-sample reservoir in fluid communication with at least one of the channels, said sample reservoir capable of releasing a fluid; and c) at least one waste reservoir in fluid communication with at least one of the channels, said waste reservoir capable of receiving a fluid.

In yet another embodiment of this invention, there are provided systems for carrying out analysis. In exemplary embodiments, these include: A) a nanofluidic chip, including: a) nanochannel array, including: a substrate having a surface, a plurality of parallel channels in the material of the surface, said channels having a trench width of less than about 150 nanometers and a trench depth of less than 200 nanometers; at least one of the channels being surmounted by sealing material to render such channels at least substantially enclosed; at least one of the channels capable of admitting a fluid; and b) at least one sample reservoir in fluid communication with at least one of the channels, said sample reservoir capable of releasing a fluid; and B) a data processor.

In another embodiment, methods of analyzing at least one macromolecule are described which, for example, include the steps of: providing a nanofluidic chip, including: a) nanochannel array, including: a surface having a plurality of parallel channels in the material of the surface, said channels having a trench width of less than about 150 nanometers and a trench depth of less than 200 nanometers; at least one of the channels being surmounted by sealing material to render such channels at least substantially enclosed; at least one of the channels capable of admitting a fluid; b) at least one sample reservoir in fluid communication with at least one of the channels, said sample reservoir capable of releasing a fluid containing at least one macromolecule; providing the at least one sample reservoir with at least one fluid, said fluid comprising at least one macromolecule; transporting the at least one macromolecule into the at least one channel to elongate said at least one macromolecule; detecting at least one signal transmitted from the at least one elongated macromolecule; and correlating the detected signal to at least one property of the at least one macromolecule.

Cartridges including a nanofluidic chip in accordance with this invention are also disclosed herein. Such cartridges are capable of being inserted into, used with and removed from a system such as those shown herein. Cartridges useful with analytical systems other than the systems of the present invention are also comprehended by this invention.

BRIEF DESCRIPTION OF THE DRAWINGS

FIG. 5 illustrates a nanofluidic chip.

FIG. 7a is scanning electron micrograph of the substrate used is Example 1 prior to sealing with silicon dioxide.

FIG. 7b is a scanning electron micrograph of the nanochannel array of Example 1 obtained after sealing the nanochannel array in 7a with silicon dioxide.

FIG. 7c is a scanning electron micrograph of the substrate used in Example 2 prior to sealing with silicon dioxide.

FIG. 7d is a scanning electron micrograph of the nanochannel array of Example 2 obtained after sealing the nanochannel array of 7c with silicon dioxide.

FIG. 7e is a scanning electron micrograph of the substrate used in Example 3 prior to sputtering with silicon dioxide.

FIG. 7f is a scanning electron micrograph of the nanochannel array of Example 3 obtained after sputtering the nanochannel array in 7e with silicon dioxide.

FIG. 8a illustrates sealed channel having a nanoslit in an opaque layer across the bottom of a channel.

FIG. 8b illustrates a sealed channel having a nanoslit in as opaque layer across the sealing layer, which is oriented perpendicular to the long axis of a nanochannel.

One aspect of the present invention encompasses a nanochannel array having a plurality of channels that are substantially enclosed. As shown in FIG. 1, the nanochannel array 100 has a surface 102 that contains a plurality of channels 104 in the material of the surface 106. The channels 104 have a wall 110, and a channel center 112. The distance between the wall surfaces 110 inside a channel 104 that are perpendicularly opposite to the channel center 112 is defined as the trench width. The channels 104 are surmounted by a sealing material 108 that renders the channels 104 at least substantially enclosed.

Figure 1:
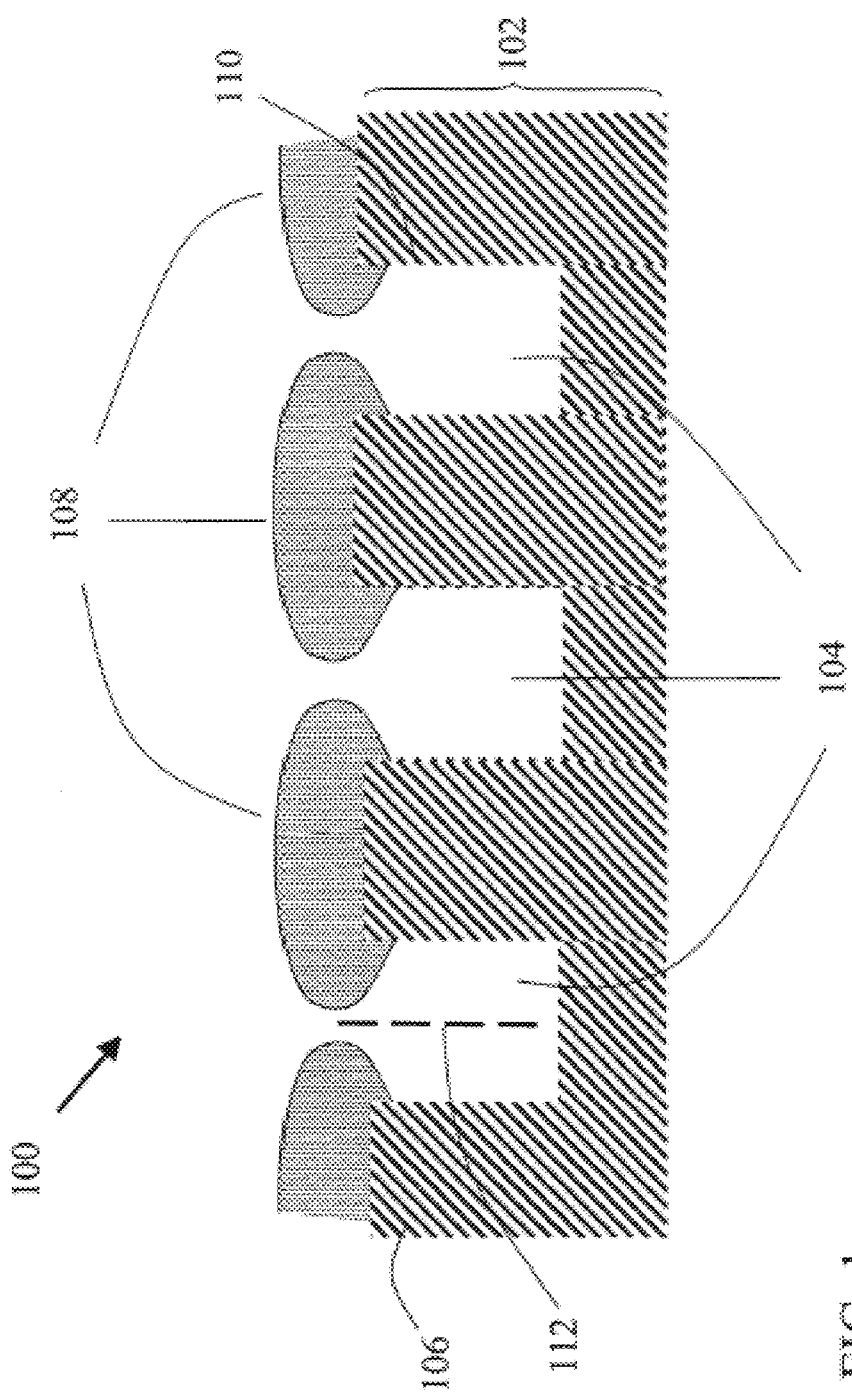
FIG. 1 illustrates a cross-section of a nanochannel array having substantially enclosed channels.
Figure 2:
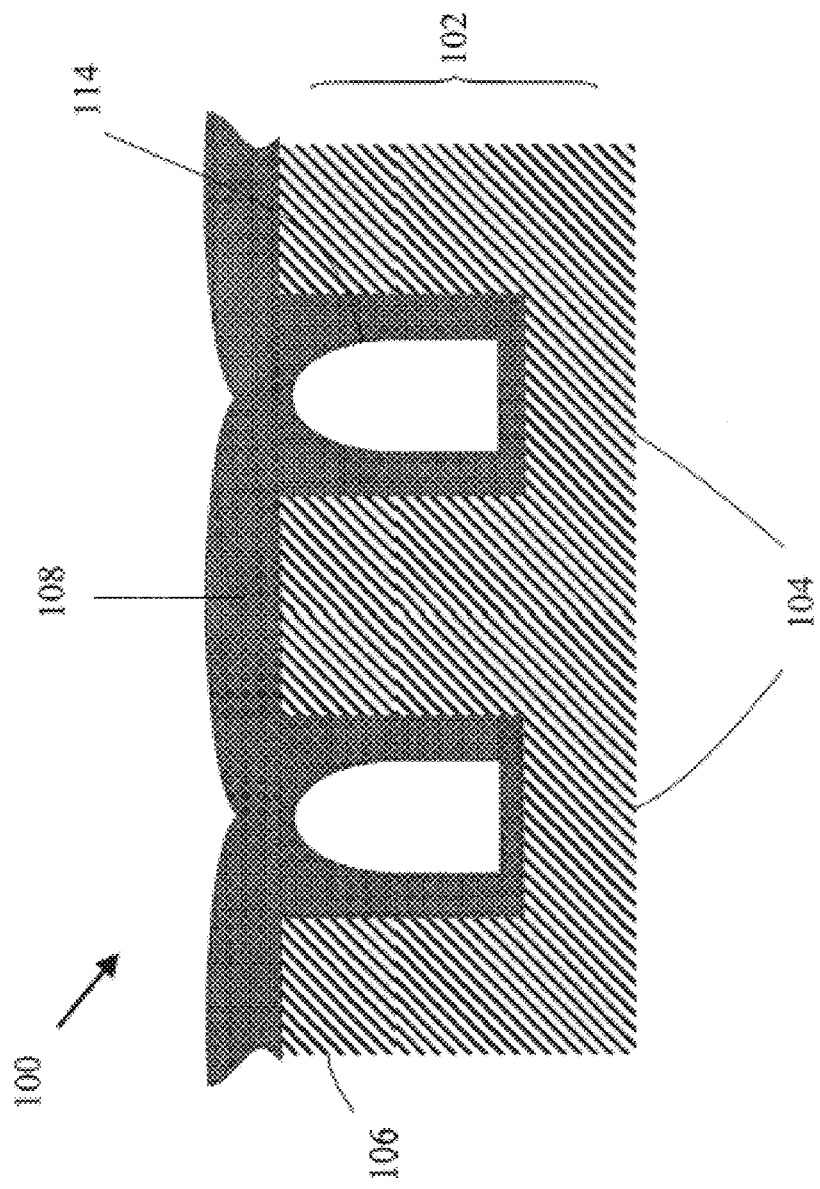
FIG. 2 illustrates a cross-section of a nanochannel array having completely enclosed channels and having sealing material deposited to the channels.

In one embodiment, the channels 104 will not be completely enclosed and will typically have no sealing material 108 directly above the channel center 112, providing an opening in the sealing material to the channel. The opening may have a variety of shapes. The size of the opening is defined as the minimum distance spanning the opening above the channel center 112. In such embodiments, the size of the opening is less than the trench width, and is typically less than ½ of the trench width, more typically less than ⅓ of the trench width, and most typically less than ¼ of the trench width. In other embodiments the channels can be completely enclosed, having sealing material completely covering the top of the channel and having no opening in the sealing material. In certain embodiments of the present invention, sealing material 108 can extend over the walls 110 and the bottom of the channels 104, as shown in FIG. 2. In such embodiment the trench width is defined as distance from the surfaces formed by the sealing material adjacent to the walls 114.

In the present invention, the trench width is typically less than 150 nanometers, more typically less than 100 nanometers, and even more typically less than: 75, 50, 25, and 15 nanometers. In certain embodiments the trench width is about 10 nanometers. In the present invention, the trench width is at least 2 nm, and typically at least 5 nm.

In the present invention the channels are at least substantially enclosed. "At least substantially enclosed" means that the channels are completely enclosed or have an opening in the sealing material that is smaller than ½ the trench width, or have both completely enclosed channels and openings.

Channels that are completely enclosed have a trench depth that is defined as the distance between the surface of the solid material at the bottom of the channel below the channel center 112 to the sealing material above the channel center 112. Embodiments in which the channels having an opening have a trench depth defined as the distance from the surface of the solid material at the bottom of the channel below the channel center to the position of the opening where the opening size is measured. If the opening has more than one position where a minimum distance can be measured then the position of the opening is the one that is closest to the bottom of the channel 104.

In the present invention, the trench depth is less than 200 nm. In certain embodiments, the trench depth is typically less than 175 nm, and more typically less than 150 nm, 125 nm, 100 nm, 75 nm, 50 nm, and 25 nm. In certain embodiments the trench depth is about 15 nm. In certain embodiments the trench depth is at least 2 nm, typically at least 5 nm, and more typically at least 10 nm.

Figure 3:
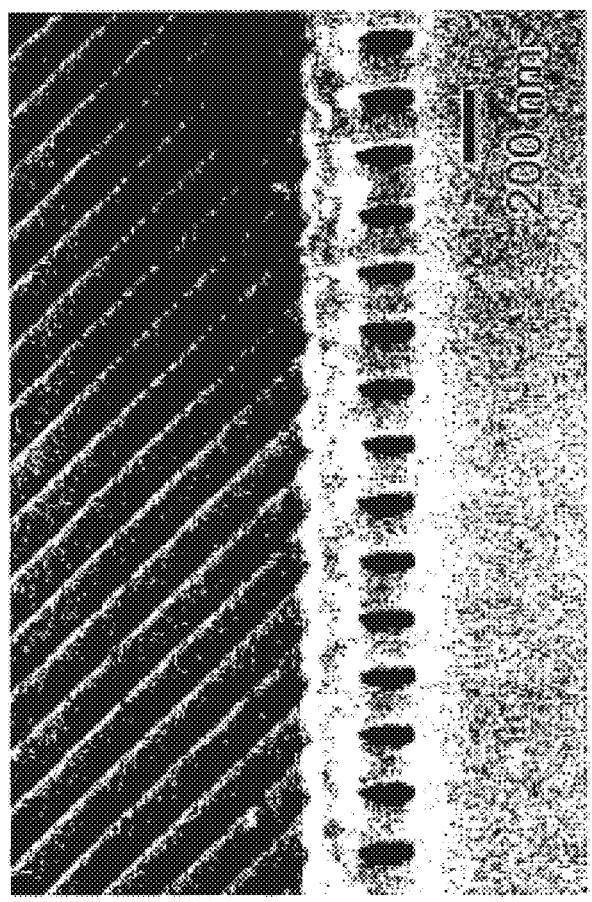
FIG. 3 is a scanning electron micrograph of a nanochannel array having parallel linear channels and open channel ends.

In the present invention, the nanochannel arrays can be formed in a substrate, such as a silicon wafer substrate, using a variety of fabrication methods as described below. In one embodiment, the nanochannel array has a plurality of parallel linear channels across the surface of substrate as illustrated by the scanning electron micrograph in FIG. 3.

In certain embodiments, the nanochannel arrays have at least one end of at least one of the channels can be in fluid communication with at least one reservoir. In these embodiments, at least one channel is connected directly with at least one reservoir. Alternatively, at least one channel can be connected with at least one reservoir via an interconnecting straight or curved microchannel (a channel having a width, height, or both larger than about a micron), or a channel is connected with at least one reservoir via an interconnecting nanopillar or micropillar array.

In certain embodiments, at least two ends of some of the channels are in fluid communication with at least one reservoir common to the channels. In these embodiments, at least two ends of some of the channels can be adjacent or not adjacent. These channels can be connected directly with at least one reservoir.

In certain embodiments, at least two channels can be connected with at least one reservoir via a common interconnecting straight or curved microchannel. Alternatively, at least two channels can be connected with at least one reservoir via a common interconnecting nanopillar or micropillar array.

In certain embodiments of the present invention, the nanochannel array has a plurality of channels that are in fluid communication with at least one sample reservoir common to at least some of the channels. By "a plurality of channels" is meant more than two channels, typically more than 5, and even typically more than 10, 100, 1000, 10,000 and 100,000 channels. In certain embodiments, one sample reservoir can be provided for all of the channels in the nanochannel array, thus the plurality of channels can be as large as the number of channels that are on the substrate. In a certain embodiments, 100 mm diameter substrates can have about 500,000 parallel linear channels having a periodicity of 200 nm, the periodicity being defined as the distance between the middle of two adjacent channels.

In certain embodiments, the plurality of channels can be connected directly with at least one reservoir. The connections can the a common interconnecting straight or curved microchannel. In other embodiments, a plurality of channels can be connected with at least one reservoir via a common interconnecting nanopillar or micropillar array.

In certain embodiments of the present invention, the nanonanochannel array contains a plurality of channels that are in fluid communication with at least one waste reservoir. Although the plurality of channels is typically connected directly with at least one waste reservoir, more than one waste reservoir can also be provided. It should be appreciated that the waste reservoir can be used as a sample collection reservoir. Accordingly, multiple sample collection reservoirs can also be provided on nanochannel arrays. In these embodiments, a plurality of channels can be connected with at least one waste reservoir via a common interconnecting straight or curved microchannel as described earlier. Likewise, a plurality of channels can be connected with at least one waste reservoir via a common interconnecting nanopillar or micropillar array.

In certain embodiments of the present invention, the nanochannel array has a plurality of channels that are substantially parallel, in which the plurality of channels are substantially in the plane of the surface of the substrate.

In certain embodiments of the present invention, the nanochannel array can contain linear channels. Linear channels are adjacent channels that are substantially not interconnected.

In certain embodiments, the ends of the channels are capable of admitting a macromolecule in a fluid. By being capable of admitting macromolecule means that the channels have at least one opening large enough to permit the passage of a macromolecule. While a variety of openings are envisages, typically such openings can be located at the ends of the channels or on the surface of the sealing material through openings in the sealing material. Openings in the sealing material can be provided by subsequent modification of the nanochannel arrays as provided below.

In certain embodiments of the present invention, the nanochannel array contains channels that are capable of transporting a macromolecule across their length. The nanochannel arrays can be fitted with a variety of components to affect macromolecular transport, examples of which include pressure or vacuum gradient drop across the channels, electroosmosis, and electrokinesis.

While not being bound to a particular theory, it is believed that macromolecules typically have a non-linear, three-dimensional conformation in space (e.g., linear polymers have a random coil conformation in their natural state). Accordingly, it is thermodynamically unfavorable for macromolecules to spontaneously elongate and enter channels directly from the environment due to the large free energy needed to reduce entropy. For example, a 169 kilobase T4 phage double stranded genomic DNA chains will form a Gaussian coil of radius of gyration $Rg=(Lp/6)^{1/2}=700$ nm in free solution, where L is its calculated contour length, and p is the persistence length of about 50 nm.

In certain embodiments, the nanochannel array can contain channels capable of transporting at least one macromolecule across the length of channels, in which the macromolecule is in an elongated form. Such channels can have openings large enough to permit the entrance of the ends of the macromolecules. In certain embodiments, it is preferred that such channels also have trench widths and trench depths narrow enough to restrict the movement of the macromolecules to primarily one direction along the surface of the substrate. Preferably such channels are not interconnected.

In certain preferred embodiments of the present invention, the nanochannel array is capable of transporting at least one biopolymer across the length of said channels. In these embodiments, the geometry of the channels permits the biopolymers to enter and move along the channels in at least one direction. Preferably, the channel surfaces are treated with a non-sticking agent, as described later, for preventing the adhesion of macromolecules, such as biopolymers, to the inside of the channels.

In other embodiments, it is preferred that the nanochannel array contains channels capable of transporting at least one unfolded biopolymer across the length of said channels. While not being bound by a particular theory, when the dimensions of the channels are apparently larger than the spatial conformation of the macromolecules, there is at least a partial amount of elongation of the macromolecules in the channels. When the dimensions of the channels are at the same order or below the persistence length of macromolecules, such as 50 nm for DNA the macromolecules can be sufficiently elongated in an unfolded fashion inside the channels. When the dimensions of the channels fall in between the above-mentioned two scenarios, macromolecules can be partially elongated in these channels. In this case, the macromolecules can be folded, tangled, or both folded and tangled. While it is envisaged that any macromolecule can be transported in an unfolded fashion in the channels of the nanochannel array of the present invention, a variety of suitable unfolded macromolecules include RNA, DNA, denatured unfolded peptide chains, self-assembled chemical polymers, and co-polymer chains, and other biopolymers, and combinations thereof.

In one preferred embodiment, the channel structures of the nanochannel arrays can be formed from linearly adjacent channel walls that span the substrate surface. In other embodiments, the channels can be formed from pillar structures, self-assembled polymer structures, stacked membrane layers, and nanobeads (particles inside the channels).

The surface material of the nanochannel arrays can be formed from almost any substrate material, such as a conductive material, a semiconductor material, or a non-conductive material. Examples of conductive materials include metals such as aluminum, gold, silver, and chromium. Examples of semiconductive materials include doped silicon dioxide and gallium arsenide. Examples of non-conductive materials include fused silica, silicon dioxide, silicon nitride, glass, ceramics, and synthetic polymers. The foregoing is exemplary only.

In the present invention, the surface of the nanochannel array is typically the surface of the substrate, such as the surface of a silicon wafer. Alternatively, the surface can be a film, such as one adjacently supported by a second substrate. Coating a material on to a second substrate can form films. A suitable coating process includes vapor deposition of a material onto a wafer.

In certain embodiments of the present invention, the nanochannel array includes at least one optically opaque material layer adjacent to the sealing material. The optically opaque material can be situated between the surface material and the sealing layer, it can be situated inside the channels, it can be situated on top of the sealing material, or a combination of these. While almost any opaque material that can be deposited as a layer is possible in this embodiment, Aluminum is preferred. For certain embodiments, it is desirable that the opaque layer thicknesses are less than about 50 nm thick. For embodiments containing nanoslits useful for carrying out near-field imaging of the contents of the channels, it is desirable to prepare slits smaller than 50 nm that are etched through the deposited opaque layer but not through the transparent sealing material for maintaining the integrity of the adjacent (underneath) channel. Without being bound by a particular theory, the optically opaque layer functions as a blocking mask for high-resolution near-field excitation. Without being bound to a particular theory, aluminum is particularly preferred as an opaque layer because it has the highest known skin depth of any material at the given wavelength of the excitation light source rendering the smallest thickness of the blocking layer, hence the shortest distance between the slits and the possible target molecules in channels.

In certain embodiments of the present invention, the nanochannel array has at least one near field slit feature above at least one channel. Such slits should be fabricated as close (less than about 30 nm) to the channel, as possible without compromising the integrity of the adjacent sealed channels. The thin wall of sealing material between slit opening and channels could be created by FIB milling or controlled material deposition.

In a further preferred embodiment, the nanochannel array contains sealing material adjacent to the channel bottom. Sealing material can be provided in channel bottom by depositing a suitable sealing material into the channels prior to or simultaneously with enclosing the channels.

The nanochannel arrays also preferentially have sealing material adjacent to the channel wall material. In this embodiment, the sealing material can reduce the trench width. This is particularly advantageous for preparing nanochannel arrays from a variety of substrate surfaces that contain channels wider than 150 nm in trench width and deeper than 200 nm in trench depth. In this embodiment, and as described below, sealing material can be deposited into channels by a variety of methods. One suitable method is E-beam evaporation, which creates a point source of material. In E-beam evaporation, a substrate is typically far away from the source compared to the size of the sample, and the angular distribution of the depositing material is very narrow. To achieve a non-uniform deposition the substrate is tilted at a specific angle. The channel walls partially block the deposition of sealing material (like a shadow), and most of the material is be deposited on the channel walls near the upper posture of the channel wall. Beyond a critical depth no deposition will occur as long as the substrate is tilted.

Figure 4:
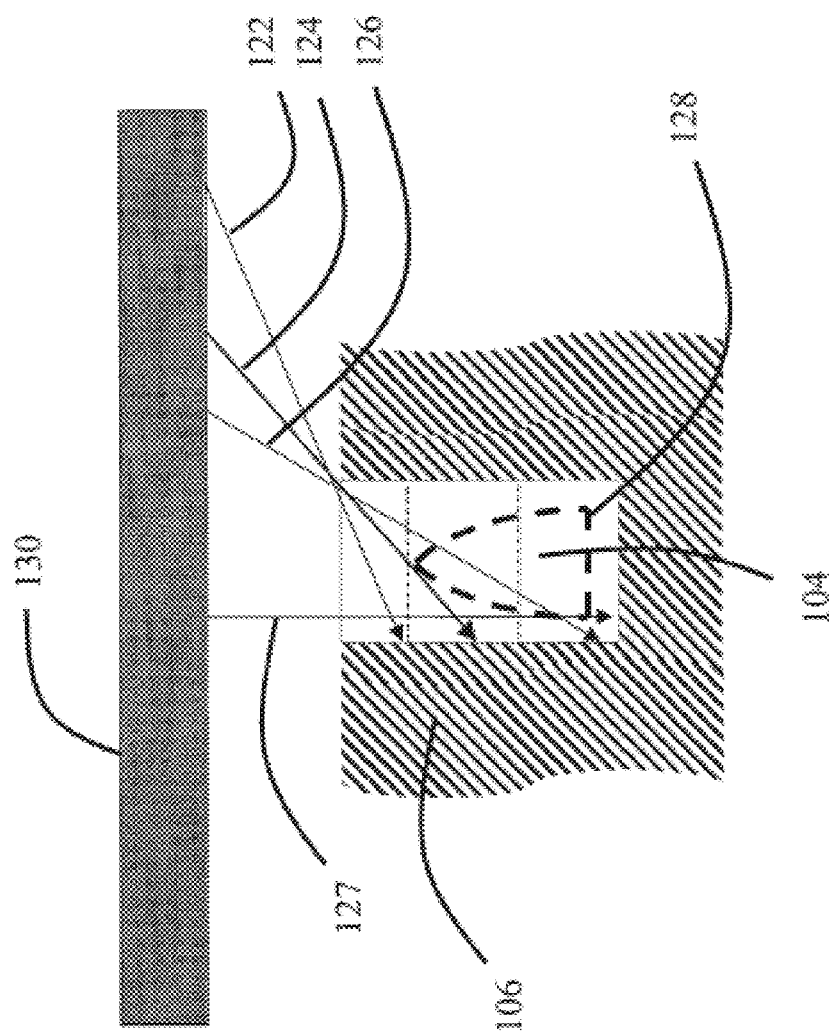
FIG. 4 illustrates a schematic of a process for depositing sealing material into the channels.

An alternative and preferred method to provide sealing material the channels is sputter deposition. In sputter deposition, the sealing material is deposited at all angles, so the instant growth rate at any point on the surface depends on the percentage of the total target area within its line of sight, as is outlined in FIG. 4. Without being bound to a particular theory, sealing material from a large target source 130 that is in close proximity to the substrate surface, can travel along a variety of trajectories (122, 124, 126, 127) and be deposited at different positions in the channels. Sputtering is typically used because of the divergent nature of the material beam, thus resulting in the faster deposition of target material at the top part of the channels instead of at the bottom of the channels (i.e., surmounting the channel). In time, the sealing material near the top of the channels eventually completely encloses the channel, which prevents further deposition of sealing material into the channel. In one embodiment, the resultant sealing material in the channel results in a profile 128. Suitable sputtering systems are known in the art. A particularly suitable sputtering system has a 200 mm SiO2 target source which provides high surface coverage and uniformity across 100 mm substrate.

The lengths of the channels of the nanochannel array can have a wide range. The lengths of the channels can also be the same or different in the nanochannel array. For carrying out macromolecular analysis using the nanochannel arrays as provided below, it is desirable that the channels are at least 1 millimeter (mm) longer. More typically, the length of the channels is greater than 1 centimeter (cm), and even greater than 5 cm, 15 cm, and 25 cm.

In another aspect, of the present invention there is provided a method of preparing a nanochannel array, which includes the steps of forming a plurality of channels in the material of the surface of a substrate, and depositing a sealing material to surmount the plurality of channels to provide at least substantially enclosed channels. Substrates containing a plurality of channels preferably have a periodicity of 200 nanometers or less, which can be provided by interferometric lithography and nanoimprint lithography techniques, which are disclosed in U.S. Pat. No. 5,772,905, the complete disclosure of which is incorporated by reference herein. As described earlier, various types of materials can be used to prepare surfaces having a plurality of channels. Suitable substrates include semiconductors, dielectrics, polymers, self-assembled biofilm, membranes, metals, alloy, and ceramics.

The sealing material is preferably deposited to surmount the plurality of channels to render such channels at least substantially enclosed, the substantially enclosed channels having a trench width of less than 150 nanometers and a trench depth of less than 200 nanometers. By "surmount" is meant that the sealing material is preferentially deposited towards the top of the channels compared to the bottom of the channels, resulting in substantially enclosed channels, which is described above and in FIG. 4.

In certain embodiments of the present invention, the sealing material can be deposited using any of a variety of methods, including chemical vapor deposition, spin coating, film lamination, and thermo-evaporation. Preferably, the sealing material is deposited using electron-beam evaporation or sputtering.

In certain embodiments of the present invention, sealing material is deposited on substrate surfaces by a sputtering process at gas pressures typically less than about 20 mTorr, more typically less than 10 mTorr, and even more typically less than 5 mTorr. Sputtering is a process of driving molecules off a source target surface (such as $SiO_2$) using energetic ionic bombardment. Atoms are knocked off from the source target and can be deposited on a variety of substrate surfaces, such as patterned silicon wafers. While not being bound to a particular theory, it is believed that as the gas pressure is reduced, there are fewer particles in the environment of the plasma sputtering chamber, which results in the depositing atoms to travel with fewer collisions before reaching the substrate surface; hence, a more anisotropic and faster deposition. At higher gas pressure such as 30 mTorr, depositing atoms collide more frequently on their path to the substrate surface, hence a more divergent traveling angles and more isotropic and slower deposition. At lower gas pressure with more anisotropic and fast deposition, more depositing atoms can reach the bottom and lower part of the sidewalk of the trenches, causing relatively faster deposition of sealing material at the bottom and sidewalk comparing to the top of the trenches, this subsequently leads so smaller channel (trench) dimensions.

The aspect ratio of the trenches being sealed also affects the geometry of the final sealed void space. The higher the depth to width ratio, the less sealing material will be deposited near the bottom of the trench. The lower the depth to width ratio, the smaller and narrower the channel dimensions.

In one embodiment of carrying out the method of the present invention, at least one reservoir is provided to the in fluid communication with at least one end of at least one of the channels. Channels can be fabricated on the substrate using nanoimprinting and interconnecting structures of pillar arrays. Reservoirs can be defined using photolithography and subsequently pattern transferred to the substrate using Reactive Ion etching (RIE), chemical etching or FIB milling directly to create reservoirs in fluid communication with the channels. Auxiliary structures, such as microchannels, for connecting the reservoirs to the channels can also be provided using these methods. Typical depth of the reservoirs and auxiliary structures is typically at least several hundreds of nanometers, preferably at least several micrometers deep.

In certain embodiments, it is desirable to provide an additional sealing step. A suitable additional sealing step includes application, of a planar surface substrate to the top of the sealing material. Alternatively, reservoirs can be formed on the sealing planar substrate. Auxiliary fluid communicating structures larger than about a micron can also be formed to connect to larger sample reservoir. A variety of schemes to connect reservoirs to the channels can be envisioned: at least 2 reservoirs can be provided in fluid communication with at least 2 separate channels; or at least 10 reservoirs are provided in fluid communication with at least 10 separate channels; or at least 96 reservoirs are provided in fluid communication with at least 96 separate channels; or at least 500 reservoirs are provided in fluid communication with at least 500 separate channels; or at least 5000 reservoirs are provided in fluid communication with at least 100 separate channels; or combinations thereof.

In a preferred embodiment of the present invention, the method of preparing the nanochannel arrays is carried out using linear channel array substrates having a periodicity of less than 200 nm formed by nanoimprint lithography. In this embodiment, the linear channels have a trench width less than 100 nanometers and a trench depth less than 100 nanometers. In this embodiment, at least a portion of the sealing material is deposited using sputter deposition to provide sealing material adjacent to the channel wall material to narrow the trench width.

Varying the sealing material deposition parameters is also used to narrow the trench width of the channels. The deposition parameters can be varied to provide trench widths of typically less than 100 nanometers. As more material is deposited, trench widths can be narrowed to less than 75 nanometers, and even less than: 50 nanometers, 25 nanometers, and 15 nanometers. Trench widths of about 10 nm can also be provided by the methods of the present invention. Typically, the resulting trench widths after deposition will be greater than 2 nm, and more typically greater than 5 nanometers. Trench depths of less than 175, 150, 125, 100, 75, 50, and 25 nm can also be provided by the methods of the present invention. Trench depths of about 15 nm can also be provided. Typically, the trench depths will be at least 5 nm, and more typically at least 10 nm.

In another embodiment of the present invention, the method may also include the step of providing at least one near field slit feature above at least one channel. In this step, the sealing material is typically transparent, such as silicon dioxide, to permit spectroscopic detection of fluorescently labeled macromolecules, such as DNA, inside the channels. This permits the use of optical methods, such as near-field optical imaging, to analyze macromolecules in the channels. Nanochannel arrays suitable for near-field optical analysis can be modified to have nanoslits. As described above, the nanoslit above the channel is thin to permit sufficient evanescent excitation of the fluorescently-labeled macromolecules.

In one embodiment of the present invention, nanochannel arrays can be prepared having a sufficiently thin seal thickness suitable, for near-field optical analysis of fluids in the channels beneath the sealing material. In one embodiment, channels having an opaque sealing material thicker than 100 nm can be modified using a suitable fabrication method to provide a nanoslit in the opaque sealing material.

Suitable fabrication methods for removing material from small area include E-beam lithography and Focus Ion Beam milling. E-beam lithography involves the lithography of ebeam resists followed by development and reactive ion etching. Focus Ion Beam (FIB) milling is preferably used, as it requires fewer steps then E-beam lithography. FIB uses a beam of energetic ions such as Gallium ions to sputter material away and is capable of resolution down to 20 nm and can etch down many microns in principle. FIB is preferred as it enables one to image the milled area immediately after FIB milling the nanoslit structure.

In one embodiment of the present invention, a portion of the sealing material can be deposited inside the channels to form at least one of: an insulating layer, a conducting layer, a hydrophilic layer, a hydrophobic layer, or combinations thereof. In this embodiment, the layer thickness typically less than half of the trench width.

In one embodiment, the dimensions, geometry, composition, or combinations thereof, of the sealing material adjacent to the walls 114 can be modified and manipulated for corresponding samples being analyzed in the channels. In a particular embodiment, it is desirable to alter the surface properties of the sealing material adjacent to the wall 114. This is carried out by treating at least some of the channels with a surface modifying agent to alter the surfaces interior to said channels.

In one embodiment, surface-modifying agents are deposited in the channels to improve the transport of macromolecules into and through the channels. Surface modifying agents are particularly useful where the internal dimensions (trench depth, trench height, or both) are less than about 50 nm. Surface-modifying agents can also reduce or increase hydrophobicity of the surfaces interior to said channels. Nanochannel arrays made according to the present invention can be contacted with solutions containing surface-modifying agents, such as by submerging the nanochannel array into such solutions. Suitable surface-modifying agents include polyethylenglycol (PEG), surfactants, Bovin Serum Albumin (BSA) protein solution, surface non-specific binding saturation, and anti-protein sticking agents. Application of a pressure differential, such as vacuum, can be used to assist the treatment of the channels. Application of vacuum is also useful for degassing any fluids inside the channels.

In certain embodiments of the present invention, the surface-modifying agent counteracts the electroosmosis effects inside the channels. While not being bound to a particular theory, the electroosmosis effect is usually due to ionized acidic groups immobilized to the matrix (e.g., attached to the wall) inducing positively charged counter ions in the buffer that migrate towards the negative electrodes, causing a bulk flow of liquid that migrates in the direction opposite to that of the negatively charged DNA. Accordingly, reducing electroosmosis effects helps charged macromolecules to be transported into and along the channels.

In one embodiment of the present invention, the channels can be at least substantially enclosed on the surface of the substrate and substantially open on the edges of the substrate. As described herein, the channels are at least substantially enclosed by controlling the deposition of the sealing material. In one embodiment, the channels are substantially open at the edges, which are readily provided by cleaving or cutting the substrate to reveal the interior portion of the channels.

In one embodiment, the deposition of the sealing material completely encloses the plurality of channels. In this embodiment, the sealing layer is at least as thick as the atoms of the sealing material. Typically, the sealing material surmounting the plurality of channels is less than 500 nanometers thick. In certain embodiments, the sealing material surmounting the plurality of channels can be less than: 100 nm, 50 nm, 25 nm, 10 nm, and 5 nm thick. Typically the sealing material surmounting the plurality of channels is at least 1 nanometer thick, and more typically at least 2 nm thick. In certain embodiments of the present invention, a step of removing a portion of the sealing material is used to reduce the thickness of the sealing material above at least one channel. Sealing material can be removed by a variety of etching and ebeam deposition methods as further described herein.

In another aspect of the present invention, there is provided a nanofluidic chip that includes a nanochannel array of the present invention. Referring to FIG. 5, the nanofluidic chip 200 has a nanochannel array 100, a substrate 146, and reservoirs 144 for samples and waste (or sample collection). Further provided in FIG. 5 are auxiliary sample ports 140 and auxiliary waste ports 142 for handling fluid sample. The reservoirs are in fluid communication with at least one of the channels, so that the sample reservoirs are capable of releasing a fluid into the channels, and the waste reservoirs are capable of receiving a fluid from the channels. Typically the fluids contain macromolecules for analysis.

In certain embodiments of the present invention, the nanofluidic chip contains at least one sample reservoir is formed in the surface of the substrate. Steps to form reservoirs in nanochannel array substrates are provided above. In this embodiment, at least one waste reservoir in fluid communication with at least one of the channels. Typically, the nanofluidic chip contains at least 1 sample reservoir. A variety of other embodiments include at least 96 reservoirs, and even at least 1000 reservoirs in the nanofluidic chip.

For use in macromolecular analysis, it is preferred that the nanofluidic chip provides at least a portion of the nanochannel array capable of being imaged with a two-dimensional detector. Imaging of the array is provided by presenting the sealing material face of the nanochannel array to suitable apparatus for the collection of emitted signals, such as optical elements for the collection of light from the nanochannel array. In this embodiment, the nanofluidic chip is capable of transporting a plurality of elongated macromolecules from a sample reservoir and across the channels.

In certain embodiments of the present invention, the nanofluidic chip contains an apparatus for transporting macromolecules from the sample reservoirs, through the channels, and into the waste reservoirs. A suitable apparatus includes at least one pair of electrodes capable of applying an electric field across at least some of the channels in at least one direction. Electrode metal contacts can be integrated using standard integrated circuit fabrication technology to be in contact with at least one sample and at least one collection/waste reservoir to establish directional electric field. Alternating current (AC), direct current (DC), or both types of fields can be applied. The electrodes can be made of almost any metal, and are typically thin Al/Au metal layers deposited on defined line paths. Typically at least one end of one electrode is in contact with buffer solution in the reservoir.

In certain embodiments of the present invention, the nanofluidic chip contains at least two pair of electrodes, each providing an electric field is different directions. In this embodiment, adjacent clusters of channels connect individual isolated reservoir. With at least two sets of independent electrodes, field contacts can be used to independently modulate the direction and amplitudes of the electric fields to move macromolecules at desired speed or directions.

In another aspect of the present invention, there is provided a system (FIG. 10, 300) that is suitable for carrying out macromolecular analysis. In the present invention, the system includes a nanofluidic chip as described herein, and an apparatus for detecting at least one signal transmitted from one or more fluids in the nanochannel array of the nanofluidic chip.

Figure 10:
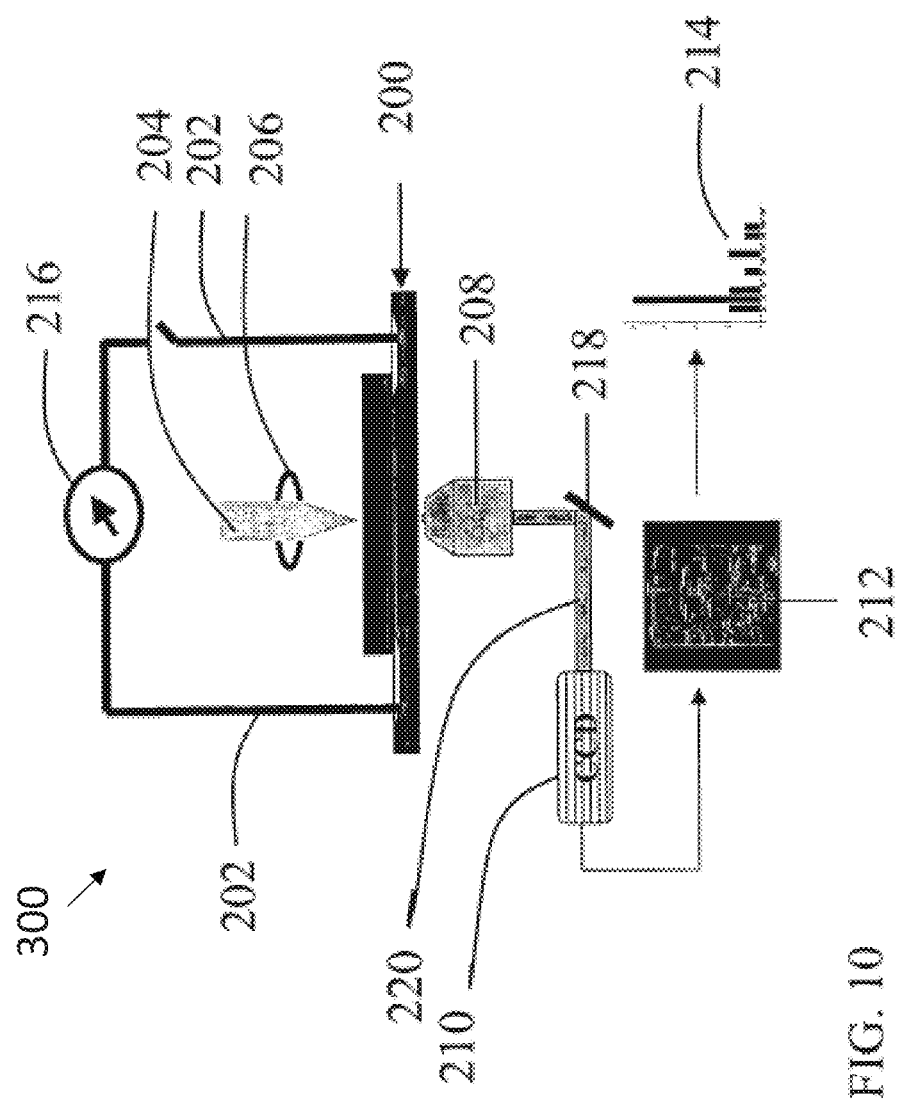
FIG. 10 illustrates a system for analyzing macromolecules using a nanofluidic chip.

In various embodiments of the present invention, the system further includes at least one of the following: a transporting apparatus to transport a fluid through at least one of the channels; a sample loading apparatus for loading at least one fluid to the sample reservoirs in the nanofluidic chip; and a data processor. The various components of the system 300 are connected together, and the general principles of operation are illustrated in FIG. 10.

The nanofluidic chip 200 used in the system is typically disposable, individually packaged, and having a sample loading capacity of 1-50,000 individual fluid samples. The nanofluidic chip typically has at least one interconnecting sample delivery microchannel to provide fluid samples into the channels, as well as sample loading openings and a reservoir, or sample loading openings and plates connected with a sealing mechanism, such as an O-ring. Metal contacts for connecting the electrodes 202 and an electric potential generator are also provided in the nanofluidic chips. Suitable metal contacts can be external contact patches that can be connected to an external scanning/imaging/electric-field tuner.

The nanofluidic chip is preferably encased in a suitable housing, such as plastic, to provide a convenient and commercially-ready cartridge or cassette. Typically the nanofluidic cartridges will have suitable features on or in the housing for inserting, guiding, and aligning the sample leading device with the reservoirs. Insertion slots, tracks, or both can be provided in the plastic case.

Macromolecular fluid samples that can be analyzed by the system includes fluids from a mammal (e.g., DNA, cells, blood, biopsy tissues), synthetic macromolecules such as polymers, and materials found in nature (e.g., materials derived from plants, animals, and other life forms). Such fluid samples can be managed, loaded, and injected using automated or manual, sample loading apparatus of the present invention.

In one embodiment of the present invention, the system includes an apparatus to excite the macromolecules inside the channels and detect and collect the resulting signals. A suitable apparatus is illustrated in FIG. 10: a laser beam 204 is focused using a focusing lens 206 to a spot on the nanochannel array 100. The generated light signal from the macromolecules inside the channels (not shown) is collected by a collection lens 208, and reflected off a dichroic mirror 218 into an optical path 220, which is fed into a CCD (charge coupled device) camera 210. Various optical components and devices can also be used in the system to detect optical signals, such as digital cameras, PMTs (photomultiplier tubes), and APDs (Avalanche photodiodes).

In another embodiment of the present invention, the system includes a data processor. The data processor can be used to process the signals from the CCD to project the digital image of the nanochannel array on a display 212. The data processor can also analyze the digital image to provide characterization information, such as macromolecular size statistics, histograms, karyotypes, mapping, diagnostics information and display the information in suitable form for data readout 214.

In another aspect of the present invention, there is provided a method of analyzing at least one macromolecule. In this invention, the analysis includes the steps of providing a nanofluidic chip according to the present invention, providing the at least one sample reservoir with at least one fluid, said fluid comprising at least one macromolecule; transporting the at least one macromolecule into the at least one channel to elongate said at least one macromolecule; detecting at least one signal transmitted from the at least one elongated macromolecule; and correlating the detected signal to at least one property of the at least one macromolecule.

In one embodiment of the present invention, the method of analyzing a macromolecule includes wetting the channels using capillary action with a buffer solution or a buffer solution containing macromolecules. Macromolecules such as polymers and DNA can introduced into nanochannel arrays by electric field.

Various macromolecules can be analyzed using the present method. For analyzing DNA typical process conditions include providing dilute solutions of DNA which are stained at a ratio of 4:1 to 10:1 base pair/dye with a suitable dye. Suitable dye stains include TOTO-1, BOBO-1, BOBO-3 (Molecular Probes, Eugene, Oreg.). Solutions of stained DNA can be further diluted and treated with an anti-oxidant and an anti-sticking agent.

In one embodiment of the present invention, the method of analyzing a macromolecule includes the sizing of one DNA. One DNA macromolecule can be extracted from a single cell or spore, such as anthrax, and suitably transported (e.g., in a polymerized gel) to avoid breakage.

Macromolecular fluid samples can be loaded through reservoirs in the nanofluidics chip and transported via interconnecting microchannels. The macromolecules are partially elongated below one end of the macromolecule enters the channels; they are substantially fully elongated when completely inside the channels. The fluorescent signals can be excited by the appropriate excitation sources and emission signals can be collected via imaging camera or detectors, in a linear scanning mode or CCD image integration. The signals collected can be analyzed by data processing software and user-defined major parameters (intensity/photons, major axis, minor axis, background signal) can be recorded and measured.

The length of a single DNA can be detected/reported and intensity profile can be plotted. In various embodiments of the present invention, the method of analyzing a macromolecule includes correlating the detected signal to at least one of the following properties: length, conformation, and chemical composition. Various macromolecules that can be analyzed this way include, biopolymers such as a protein, a polypeptide, and a nucleic acid such as RNA or DNA For DNA nucleic acids, the detected signals can be correlated to the base pair sequence of said DNA.

The typical concentration of the macromolecules in the fluid will be one macromolecule, or about at least attogram per ml, more typically at least one femtogram per ml, more typically at least one picogram per ml, and even more typically at least one nanogram per ml. Concentrations will typically be less than 5 micrograms per milliliter and more typically less than 0.5 micrograms per milliliter.

In one embodiment of the present invention, the method of analyzing a macromolecule measures the length of macromolecules having an elongated length of greater than 150 nanometers, and typically greater than 500 nanometers, 1 micron, 10 microns, 100 microns, 1 mm, 1 cm, and 10 cm long.

DNA having greater than 10 base pairs can also be analyzed using the present methods. Typically, the number of base pairs measured can be greater than 100 base pairs, greater than 1,000 base pairs, greater than 10,000 base pairs, greater than 20,000 base pairs, greater than 40,000 base pairs, and greater than 80,000 base pairs. DNA having more than 1 million, 10 million, and even 100 million basepairs can be analyzed with the present methods.

In one embodiment of the present invention, the methods can be used to analyze one or more of the following: restriction fragment length polymorphism, a chromosome, and single nucleotide polymorphism.

The following abbreviations are used herein: "nm" is nanometer, "mTorr" is milli Torr.

GENERAL PROCEDURES

After NIL and etching, non-uniform deposition of sealing material was provided by e-beam evaporation with a tilted sample wafer at various angles or sputter deposition using a large source target. This step was used to both reduce the trench width and seal the channels.

Generally, 100-340 nm of $SiO_2$ was deposited onto the patterned substrate. Effective sealing was achieved with various deposition conditions that were tested. At gas pressure of 30 mTorr, RF power of ~900 W, and DC bias of 1400 V, a deposition rate of ~9 nm/min was achieved. At lower pressure of 5 mTorr, the deposition rate was increased to an estimated 17 nm/min. Sealing material was deposited on the patterned substrate by sputtering at 5 mTorr.

EXAMPLES

In the following examples, nanochannel arrays were prepared using a process to deposit $SiO_2$ sealing material on patterned substrates by sputtering. Channel openings were prepared by cleaving the substrate and imaged by Scanning Electronic Microscope (SEM). Results are as follows and shows that the trench widths are narrowed by the deposition of the sealing material using sputtering:

Example 1

A 100 mm silicon substrate was provided having a plurality of parallel linear channels that had an 85 nm trench width and a 200 nm trench height (FIG. 7a). This substrate was sputtered at a gas pressure of 5 mTorr according to the general procedures given above. After sputtering, the channels had a 52 nm trench width, a 186 nm trench height, and a seal thickness of 200 nm (FIG. 7b). Apparently, the trench height increased slightly as a result of the sealing process forming a cone-shaped seal above the channel.

Example 2

A patterned substrate having a 65 nm trench width and about 100 nm trench height prior to sputtering formed a nanochannel array having a 17 nm trench width, a 68 nm trench height, and a channel seal thickness of about 350 nm. Sputtering gas pressure was 5 mTorr.

Example 3

A patterned substrate having a 50 nm trench width and about 80 nm trench depth prior to sputtering formed a nanochannel array having a 18 nm trench width, 51 nm trench height, and a channel seal thickness of 350 nm. Sputtering gas pressure was 5 mTorr.

Example 4

Figure 6A:
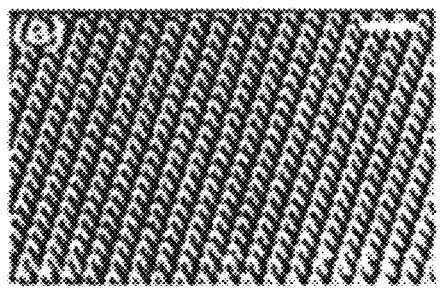
FIG. 6a is a scanning electron micrograph of the substrate used in Example 4 prior to sealing with silicon dioxide.
Figure 6B:
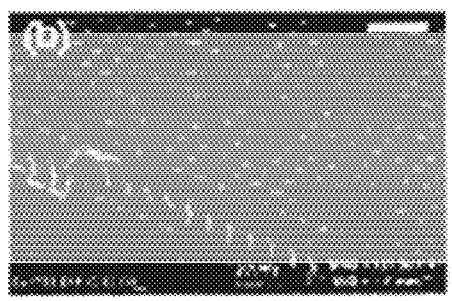
FIG. 6b is a scanning electron micrograph of the nanochannel array of Example 4 obtained after sealing the substrate with silicon dioxide.
Figure 6C:
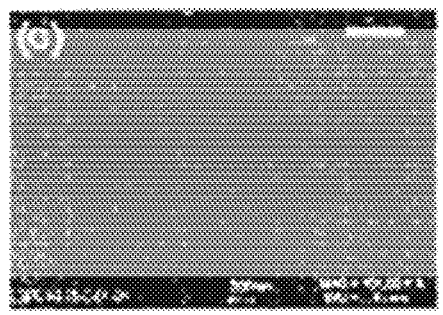
FIG. 6c is a scanning electron micrograph (top view) of the nanochannel array of Example 5.
Figure 6D:
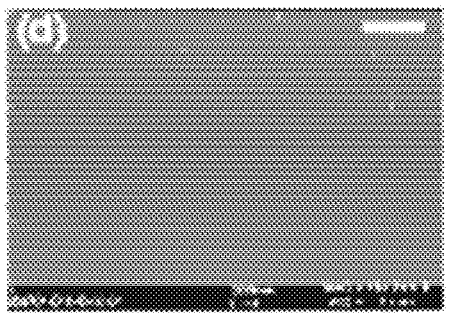
FIG. 6d is a scanning electron micrograph (top view) of the nanochannel array of Example 4.

A substrate containing a two-dimensional array of pillars was made using a two-step NIL process with the channel mold rotated 90° between the imprinting steps (FIG. 6a). The pillar array structure is subsequently completely sealed with silicon dioxide using a 29 minute deposition time. The seal thickness was about 500 nm. A profile view of the channel is depicted in FIG. 6b and a top view of the completely sealed nanochannel array is depicted in FIG. 6d.

Example 5

Example 4 was repeated except the sputter deposition time was 17 minutes to provide a nanochannel array that is not completely sealed. A top view scanning electron micrograph of this nanochannel array is provided in FIG. 6d. The seal thickness was 300 nm.

Example 6

A nanoslit 120 is provided in a channel prepared with a silicon dioxide sealing material for carrying out near-field analysis having a seal thickness greater than about 100 nm is modified by using FIB to create a nanoslit 120 having a thickness less than 100 nm. FIG. 8 shows a schematic of how the deposited sealing material on a nanochannel array is first milled away using FIB from the sealing material situated above the sealed channels. Subsequently, aluminum is deposited to create an opaque layer 116, 118 to provide optical contrast at the slit.

Example 7

This example shows how a nanochannel array can be prepared from a substrate having a plurality channels larger than 150 nm wide by 150 nm deep. A substrate is prepared by photolithography techniques to provide a plurality of channels with width of greater than 1.5 micron using conventional optical lithography techniques: Contact aligner such as Karl Suss MA-6 to provide a pattern resolution at low micron level; Industrial projection stepper. The angle of the incident depositing beam of sealing material is varied to reduce the trench width and height to less than 150 nm and 150 nm, respectively, and to substantially seal by providing shallow tangential deposition angles.

Example 8

This example provides a nanochannel array using an e-beam technique. A substrate is provided as in Example 1. Silicon dioxide is deposited by an e-beam (thermo) evaporator (Temescal BJD-1800) onto the substrate. The substrate is placed at various angles incident to the depositing beam from the silicon dioxide source target; the deposition rate is set to about 3 nm/minute and 150 nm of sealing material is deposited in about 50 minutes.

Example 9

In this example, a nanochannel array is contacted with a surface-modifying agent. A nanochannel array made according to Example 1 is submerged in a surface-modifying agents solutions containing polyethylene glycol inside a vacuum chamber overnight to facilitate wetting and treatment of the channels and degas the air bubbles that might be trapped inside the channels.

Example 10

This example shows the preparation of a nanochannel array having a metal sealing material. An e-beam (thermo) evaporator (Temescal BJD-1800) was used to deposit Chromium (Cr) onto a nanochannel array chip (trench width 80 nm, trench depth 80 nm, SiO2/Si substrate). The substrate was placed at various angles to the incident depositing beam from the source target, the deposition rate was set at 2.0-3.6 nm/minute. The resulting trench width was 20 nm, trench depth less than 80 nm, and the channels were substantially closed.

Example 11

This example shows the process of adding an optically opaque layer to a nanochannel array. A nanochannel array made according to Example 3 is placed perpendicular to the incident depositing beam, to provide an opaque layer less than 50 nm thick. An aluminum source target is selected for depositing on top of the SiO2 sealing material above the sealed channels. The deposition rate was set at 2.0-3.6 nm/minute.

Example 12

This example describes the steps seeded to provide a near-field slit in a nanochannel array. FIB was used to mill narrow slits less than 50 nm in width in the direction perpendicular to the long axis of the nanochannel array of Example 11. The depth of the FIB milling was controlled to expose the underlying thin SiO2 sealing material above the nanochannel array.

Example 13

This example describes how to provide a sample reservoir with a nanochannel array to provide a nanofluidic chip. A nanochannel array having 100 nm wide, 100 nm deep channels was made according to general procedures of Example 1. The nanochannel array was spin-coated with a photoresist and imaged with a photomask to provide regions on opposite ends of the nanochannel array. The exposed areas were etched using reactive ion etching to expose the channel ends and to provide a micron-deep reservoir about a millimeter wide on the opposite ends of the channels at the edge of the substrate.

Example 14

This example describes how to fill a nanofluidic chip with a fluid containing DNA macromolecules to analyze the DNA. A cylindrical-shaped plastic sample-delivery tube of 2 mm diameter was placed in fluid communication with one of the reservoirs of the nanochannel array of Example 13. The delivery tube is connected to an external sample delivery/collection device, which is in turn connected to a pressure/vacuum generating apparatus. The channels are wetted using capillary action with a buffer solution. A buffer solution containing stained lambda phage macromolecules (lambda DNA) were introduced into the nanochannel array by electric field (at 1-50 V/cm); the solution concentration was 5 microgram/mL and the lambda DNA was stained at a ratio of 10:1 base pair/dye with the dye TOTO-1 (Molecular Probes, Eugene, Oreg.). This solution of stained DNA was diluted to 0.1-0.5 microgram/mL into 0.5×TBE (tris-boroacetate buffer at pH 7.0) containing 0.1M of an anti-oxidant and 0.1% of a linear polyacrylamide used as an anti-sticking agent.

Example 14.1

Figure 9A:
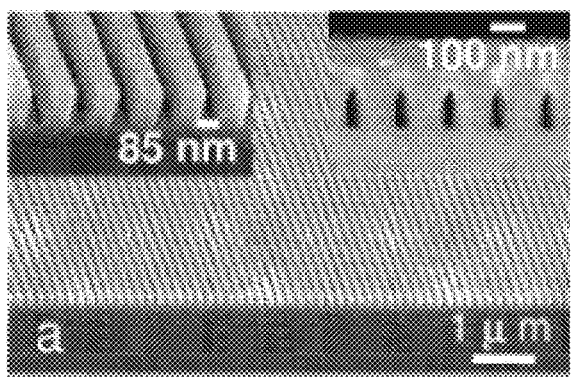
FIG. 9a shows scanning electron micrographs of the substrate (left and bottom) and a of the sealed nanochannel array (right) used in Example 14.
Figure 9C:
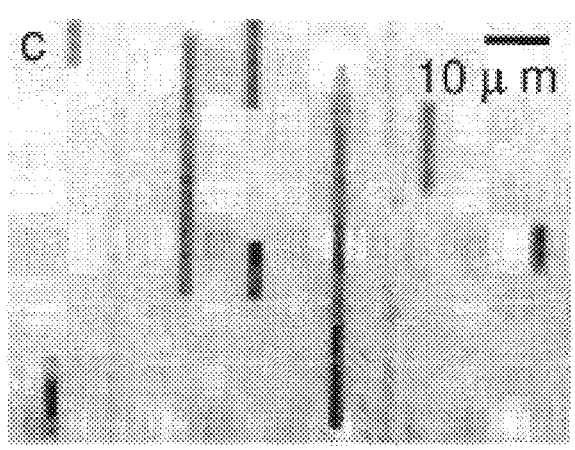
FIG. 9c shows a nanochannel array simultaneously elongating, separating, and displaying a plurality of DNA macromolecules ranging in size from 10 kb to 196 kb.
Figure 9B:
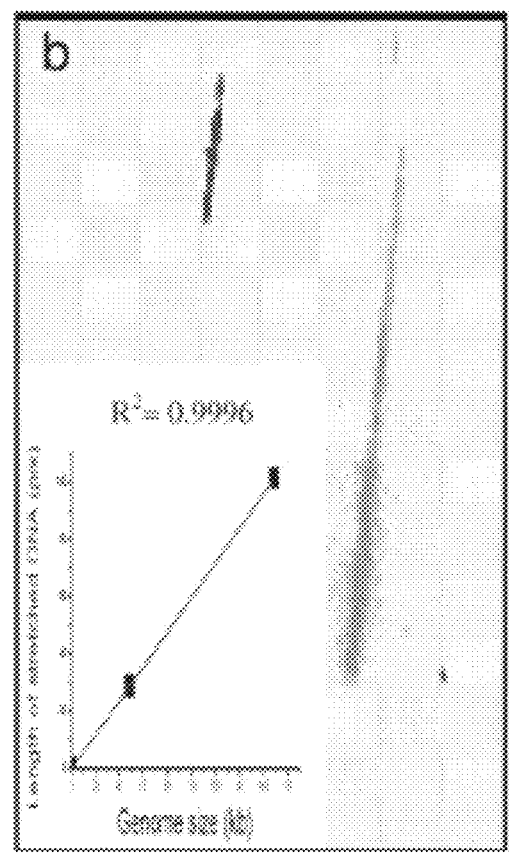
FIG. 9b is the image obtained from the CCD of the 48.5 kb lambda phage genome (shorter) and 168 kb T4 phage genome (longer) of Example 14. Inset: Plot of genome size versus macromolecular contour length.

A nanofluidic chip made according to Example 12, having channel dimensions of 100 nm×100 nm was filled using capillary action with a buffer solution containing stained genomic DNA to draw the DNA macromolecules into the channels with an electric field. Bacteria phage DNA molecules Lambda (48.5 kb) and T4 (168.9 kb) were stained with the dye TOTO-1 and BOBO-3 respectively. This solution of stained DNA was diluted to 0.5 μg/mL into 0.5×TBE containing 0.1M dithiothreatol as an anti-oxidant and 0.1% of a linear acrylamide used as an anti-sticking agent). A Nikon Eclipse TE-300 inverted microscope with a 60× (N.A.1.4) oil immersion objective was used with an Ar:K laser (Coherent Lasers) as an excitation source at 488 nm and 570 nm. A Roper Scientific Pentamax intensified cooled CCD camera with a 512×512 pixel array and 16 bits digital output was used to image the molecules. Digital image was analyzed using a data processor by NIH Image software. FIG. 9 b shows an integrated image of the stretched Lambda and T4 phage genomes side by side in the channels. The inset of 9 b shows the near perfect linear fit of the directly measured length obtained from the digital image plotted against their genome size, (R2 is 0.99996). FIG. 9 c shows an array of fluorescently-labeled genomic DNA molecules aligned and stretched in the channels with the size ranging from 10 kb to 194 kb. This shows that millions of centimeter long parallel channels could be fabricated over the whole wafer. Accordingly, the entire length of genomic DNA molecules can be stretched and analyzed.

Example 15

Example 14 is repeated, but with a 96 multiple reservoir system. A nanofluidic chip made according to Example 12 is modified with a photomask to provide 96 sample reservoirs, each reservoir connected to 1000 channels along one edge of the 100 mm substrate. 96 different DNA samples are delivered and injected using capillary fibers connected to the sample reservoirs. 96 collection reservoirs are connected to the corresponding ends of the channels to collect the DNA samples.

Example 16

This example describes a system used for carrying out analysis of macromolecules. The system contains an automated 96-capillary auto-injection sample loader to deliver 96 macromolecular fluid samples into the delivery ports of a nanofluidic cartridge. The nanofluidic cartridge is a nanofluidic chip encased by a plastic polycarbonate housing, having delivery ports and collection ports for connection to microcapillary tubing, and embedded metal contacts for connection to electrodes on the nanofluidic chip. The cartridge can be inserted in a cartridge holder, which is integrated with an a laser excitation source and suitable optical components to provide the excitation of and collection of optical signals emanating from sample fluids within the nanochannel arrays of the nanofluidic chip. The signal detection/collection apparatus is a cooled CCD digital camera. Signals from the digital camera are analyzed by a data processor using NIH image analysis software, and displayed on a monitor.

Example 17

This example describes how to use the system of Example 16 to size one DNA macromolecule. A single Anthrax spore is lysed to extract its entire genomic contents (DNA) with 10 microliters of a buffer solution and stained with fluorescent dyes. The sample loader is inserted into the delivery ports of the cartridge and injects the DNA-containing fluid. The electrodes are activated and the DNA macromolecules are transported into the nanochannel array, where they become elongated. The fluorescent stains on the DNA are excited by the excitation source, and their emission signals are collected using the CCD camera. The signals collected, analyzed and recorded for intensity and position by the data processor. The length of a single DNA is defected and intensity profile is plotted.

In another aspect of the present invention, there is provided 144. A cartridge comprising at least one nanofluidic chip, said cartridge capable of being inserted and removed from a system for carrying out macromolecular analysis, said at least one nanofluidic chip comprising at least one nanonanochannel array, said nanonanochannel array comprising a surface having a plurality of channels in the material of the surface, said channels having a trench width of less than about 150 nanometers and a trench depth of less than 200 nanometers;

at least some of the channels being surmounted by sealing material to render such channels at least substantially enclosed.

What is claimed is:

1. A method of analyzing at least one macromolecule, comprising the steps of:

transporting at least one macromolecule in a fluid sample into a nanochannel, such that the at least one macromolecule is in a fully elongated state when completely inside the nanochannel;

maintaining the at least one macromolecule in the fully elongated state within the nanochannel without application of a shear force;

detecting at least one signal transmitted from the at least one fully elongated macromolecule within the nanochannel; and correlating the detected signal to at least one property of the at least one macromolecule.

2. The method of claim 1, wherein the at least one macromolecule is transported into the nanochannel by applying an electric current.

3. The method of claim 1, wherein the trench width of the nanochannel is less than about 150 nanometers.

4. The method of claim 1, wherein the trench depth of the nanochannel is less than about 200 nanometers.

5. The method of claim 1, wherein the width of the nanochannel is substantially constant along the length of the nanochannel.

6. The method of claim 1, wherein the nanochannel is in the material of a surface.

7. The method of claim 1, wherein the nanochannel is surmounted by sealing material to render the nanochannel at least substantially enclosed.

8. The method of claim 1, wherein the at least one detected signal is correlated to at least one of the following properties: length, conformation, and chemical composition.

9. The method of claim 1, wherein the macromolecule is a synthetic polymer or biopolymer.

10. The method of claim 9, wherein the biopolymer is at least one of: a protein, a polypeptide, and a nucleic acid.

11. The method of claim 10, wherein the nucleic acid is DNA and the detected signals are correlated to the base pair sequence of said DNA.

12. The method of claim 1, wherein the at least one macromolecule has a fully elongated length in nanochannel of greater than 150 nanometers.

13. The method of claim 1, wherein the at least one macromolecule is DNA having greater than 10 base pairs.

14. The method of claim 1, wherein the at least one macromolecule is a restriction fragment length polymorphism.

15. The method of claim 1, wherein the at least one macromolecule is at least one chromosome.

16. The method of claim 15, wherein the at least one chromosome is analyzed to determine the presence of at least one single nucleotide polymorphism.

17. The method of claim 1, further comprising the step of illuminating the at least one macromolecule within the nanochannel.

18. The method of claim 7, wherein the sealing material is optically transparent.

19. The method of claim 18, wherein at least one signal is transmitted through the optically transparent sealing material.

20. A method of maintaining at least one macromolecule in fully elongated state, comprising the steps of:

transporting at least one macromolecule in a fluid sample into a nanochannel, such that the at least one macromolecule is in a fully elongated state when completely inside the nanochannel; and maintaining the at least one macromolecule in fully elongated state within the nanochannel without application of a shear force.

21. The method of claim 20, wherein the at least one macromolecule is transported into the nanochannel by applying an electric current.

22. The method of claim 20, wherein the trench width of the nanochannel is less than about 150 nanometers.

23. The method of claim 20, wherein the trench depth of the nanochannel is less than about 200 nanometers.

24. The method of claim 20, wherein the width of the nanochannel is substantially constant along the length of the nanochannel.

25. The method of claim 20, wherein the nanochannel is in the material of a surface.

26. The method of claim 20, wherein the nanochannel is surmounted by sealing material to render the nanochannel at least substantially enclosed.

27. The method of claim 20, wherein the macromolecule is a synthetic polymer or biopolymer.

28. The method of claim 27, wherein the biopolymer is at least one of: a protein, a polypeptide, and a nucleic acid.

29. The method of claim 28, wherein the nucleic acid is DNA.

30. The method of claim 20, wherein the at least one macromolecule has fully elongated length in nanochannel of greater than 150 nanometers.

31. The method of claim 20, wherein the at least one macromolecule is DNA having greater than 10 base pairs.

32. The method of claim 20, wherein the at least one macromolecule is a restriction fragment length polymorphism.

33. The method of claim 20, wherein the at least one macromolecule is at least one chromosome.

* * * * *